US008613948B2

(12) United States Patent
Barras et al.

(10) Patent No.: US 8,613,948 B2
(45) Date of Patent: *Dec. 24, 2013

(54) TREATMENT OF FAECAL INCONTINENCE AND OTHER CONDITIONS WITH 1R, 2S-METHOXAMINE

(71) Applicant: Norgine BV, Amsterdam (NL)

(72) Inventors: Norman Barras, Mid Glamorgan (GB); Jeffrey Martin Thompson, Mid Glamorgan (GB)

(73) Assignee: Norgine BV, Amsterdam ZO (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/678,131

(22) Filed: Nov. 15, 2012

(65) Prior Publication Data

US 2013/0072567 A1     Mar. 21, 2013

Related U.S. Application Data

(63) Continuation of application No. 12/586,973, filed on Sep. 30, 2009, which is a continuation of application No. 10/499,873, filed as application No. PCT/GB02/05864 on Dec. 20, 2002, now abandoned.

(30) Foreign Application Priority Data

Dec. 21, 2001 (GB) ................................. 0130763.6

(51) Int. Cl.
*A61K 9/22* (2006.01)
*A61K 31/135* (2006.01)

(52) U.S. Cl.
USPC ........................................ 424/468; 514/653

(58) Field of Classification Search
None
See application file for complete search history.

(56) References Cited

U.S. PATENT DOCUMENTS

| 4,292,300 A | 9/1981 | Byrne et al. |
| 5,116,878 A | 5/1992 | Cabanes et al. |
| 5,213,808 A | 5/1993 | Bar-Shalom et al. |
| 5,436,009 A | 7/1995 | Jauw et al. |
| 6,539,381 B1 | 3/2003 | Prasad et al. |
| 7,089,228 B2 | 8/2006 | Arnold et al. |
| 2003/0135523 A1 | 7/2003 | Brodersen et al. |

FOREIGN PATENT DOCUMENTS

| JP | 60-172953 | 9/1985 |
| WO | WO 91/00730 | 1/1991 |
| WO | WO 98/27971 | * 7/1998 |
| WO | WO 02/41920 | 5/2002 |
| WO | WO 02/080669 | 10/2002 |

OTHER PUBLICATIONS

Fujita et al. (American Chemical Society 1984, 106, 4629-4630.*
Patil et al. (Journal of Pharmacology and Experimental Therapeutics vol. 150, No. 3, pp. 445-451).*
Anibarro et al., "Allergic Contact Blepharoconjunctivitis caused by Phenylephrine Eyedrops", Contact Dermatitis, 25: 323-334 (1991).
Baeten et al., "Dynamic Graciloplasty for Treatment of Faecal Incontinence", Lancet, 338: 1163-1165 (1991).
Barlow et al., "Faecal incontinence", Gastroenterology in Practice, 18-21 (1995).
Burleigh et al., "Neural and pharmacologic factors affecting motility of the internal anal sphincter", Gastroenterology, 84 (2): 409-417 (1983).
Burleigh et al., Coloproctology and the Pelvic Floor, 2nd Edition, Chapter 3, pp. 37-53 (1992).
Carapeti et al., "Topical Phenylephrine Increases Anal Sphincter Resting Pressure", Br. J. Surg., 86: 267-270 (1990).
Carapeti et al., "Randomized, Controlled Trial of Topical Phenylephrine for Fecal Incontinence in Patients after Ileoanal Pouch Construction", Dis. Colon Rectum, 43: 1059-1063 (2000).
Cheetham et al., "Topical Phenylephrine Increases Anal Canal Resting Pressure in Patients with Faecal Incontinence", Gut, 48: 356-359 (2001).
Cook et al., "Management of Faecal Incontinence Following Obsteric Injury", Br. J. Sur., 85: 293-299 (1998).
Cook et al., "Review article: the pharmacology of the internal anal sphincter and new treatments of ano-rectal disorders", Ailment Pharmacol. Ther., 15: 887-898 (2001).
Deen et al., "Randomized Trial of Internal Anal Sphincter Application with Pelvic Floor Repair for Neuropathic Fecal Incontinence", Dis. Colon Rectum, 38: 14-18 (1995).
Enck et al., "Die Behandlung Der Analinkontinenz", Internist, 34(1): 51-58 (1993).
Fawcett et al., "Antidepressant Treatment and Chemical Sympathectomy Fail to Modulate 1-Adrenoceptor Sensitivity in Mouse Eye", Neuropharmacology, 32(12): 1373-1379 (1993).
Fraunfelder et al., "Possible adverse effects from topical ocular 10% phenylephrine", Am. J. Ophthalmol., 85: 447-453 (1978).
Fujita et al., "Highly Diastereocontrolled Reduction of Ketones by means of Hydrosilanes. Practical Synthesis of Optically Active 1,2-Diols and 2-Amino Alcohols of Threo or Erythro Configuration", J. Am. Chem. Soc., 106: 4629-4630 (1984).
Fujita et al., "Erythro-Directive Reduction of -Substituted Alkanones by Means of Hydrosilanes in Acidic Media", J. Org. Chem., 53(23): 5415-5421 (1988).
Gübitz et al., "Resolution of the Enantiomers of Drugs Containing amino Alcohol Structure after Derivatization with Bromoacetic Acid", Chirality. 4333-4337 (1992).
Gutierrez et al., Autonomic Control of the Internal Anal Sphincter in Man; In: von Trappen G. ed., International Symposium of Gastrointestinal Motility. Leuven, Belgium: Typoff Press, 363-73 (1975).
Guitierrez et al., "The Adrenergic Control of the Internal Anal Sphincter in Man", Clinical Research, 23(3): 250A (1975).
Hechtmann et al., "Moderation of anal sphincter tone with nitric oxide agonists and antagonists", Archives of Surgery, 131(7): 775-778 (1996).

(Continued)

*Primary Examiner* — Brian Gulledge
*Assistant Examiner* — Snigdha Maewall
(74) *Attorney, Agent, or Firm* — Yankwich & Associates, P.C.; Michael R. Wesolowski; Leon R. Yankwich

(57) ABSTRACT

1R,2S-Methoxamine may be used topically for effective treatment of faecal incontinence at low doses without local or systemic side effects, for example, without affecting blood pressure. 1R,2S-Methoxamine may be used to treat other disturbances and disorders of the gastro-intestinal, as a pressor agent, as a nasal decongestant and in ophthalmology, at low does and without significant side effects.

3 Claims, 14 Drawing Sheets

(56) References Cited

OTHER PUBLICATIONS

International Search Report for PCT/GB02/05864 mailed May 19, 2003.
Jorge et al., "Etiology and management of fecal incontinence", Dis. Colon Rectum, 36: 77-97 (1993).
Kamm, "Obstetric Damage and Faecal Incontinence", Lancet, 344: 730-733 (1994).
Kusonoki et al., "Usefulness of valproate sodium for treatment of incontinence after ileoanal anastomosis", Surgery, Mar., 107(3): 311-315 (1990) (Abstract only).
Madoff et al., "Fecal Incontinence", New England Journal of Medicine, Apr. 9, pp. 1002-1007 (1992).
Malouf et al., "Permanent Sacral Nerve Stimulation of Fecal Incontinence", Annals. Surg., 232(1): 143-148 (2000).
Marcio et al., "Etiology and Management of Fecal Incontinence", Dis. Colon Rectum, 36: 77-97 (1993).
Mortensen et al., "The Anal Continence Plug: A Disposable Device for Patients with Anorectal Incontinence", Lancet, 338: 295-297 (1991).
M.P. Nikolaev's Pharmacology Textbook for Students of Pharmaceutical Institutes, published 1948 by the State Medical Literature Press "Medgie", Moscow, USSR, p. 36 (Translation included).
Musial et al., "The Effect of Loperamide on Anorectal Function in Normal Healthy Men", J. Clin. Gastroenterol., 15(4): 321-324 (1992).
Nelson et al., "Community-Based Prevalence of Anal Incontinence", JAMA, 274: 559-561 (1995).
Patil et al., "Steric Aspects of Adrenergic Drugs. V. Beta Adrenergic Blocking Effects of Optical Isomers of Methoxamine and Isopropylmeyhoxamine", J. Pharmacol. Exp. Ther., 156(3): 445-451 (1967).

Rattan et al., "Role of nitric oxide as a mediator of internal anal sphincter relaxation", Am. J. Physiol, 262(1): 107-112 (1992).
Ruffolo Jr. et al., "- and β-Adrenoceptors: From the Gene to the Clinic. 2. Structure-Activity Relationships and Therapeutic Applications", J. Med. Chem., 38(19): 3681-3716 (1995).
Schröder et al., "Pharmazeutische Chemi", Georg Thieme Verlag Stuttgart, 668-673 (1982).
Smith et al., "2-Amino- and 2-Guanidino-1,2,3,4-tetrahydro-1,4-epoxynaphthalenes as Conformationally Defined Analogues of -Adrenergic Agents", J. Med. Chem., 30: 1105-1110 (1987).
Speakman et al., "Adrenergic Control of the Internal Anal Sphincter is Abnormal in Patients with Idiopathic Faecal Incontinence", Br. J. Surg., 77: 1342-1344 (1990).
Speakman et al., "The internal anal sphincter—new insights into faecal incontinence", Gut, 32: 345-346 (1991).
Speakman et al., "Decreased sensitivity of muscarinic but not 5-hydroxytrypatamine receptors of the internal anal sphincter in neurogenic faecal incontinence", Br. J. Surg., 79: 829-832 (1992).
Speakman et al., "Abnormalities of Innervation of Internal Anal Sphincter in Fecal Incontinence", Digestive Diseases and Sciences, 38(11): 1961-1969 (1993).
Vaizey et al., "Primary Degeneration of the Internal Anal Sphincter as a cause of Passive Faecal Incontinence", Lancet, 349: 612-615 (1997).
Ward et al., "Improved Cyclodextrin Chiral Phases: A Comparison and Review", J. Liquid Chromatography, 9(2 & 3): 407-423 (1986).
Yamamoto et al., "Role of alpha adrenoceptors in opossum internal anal sphincter", J. Clin. Invest., 86(2): 424-429 (1990).

* cited by examiner

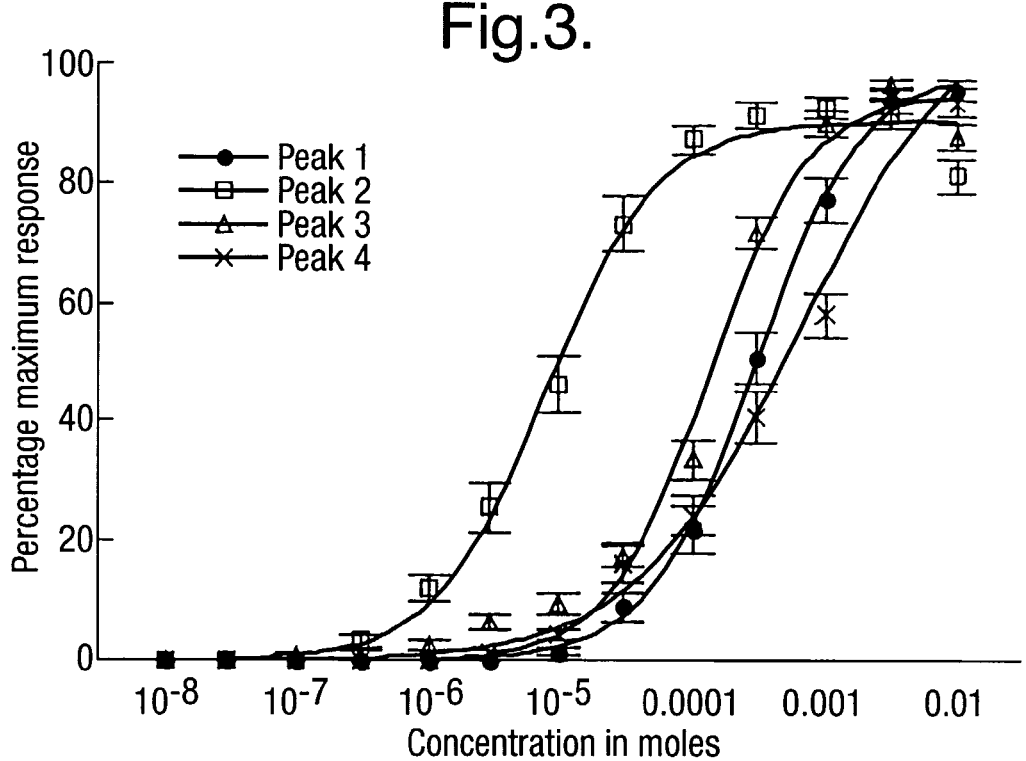
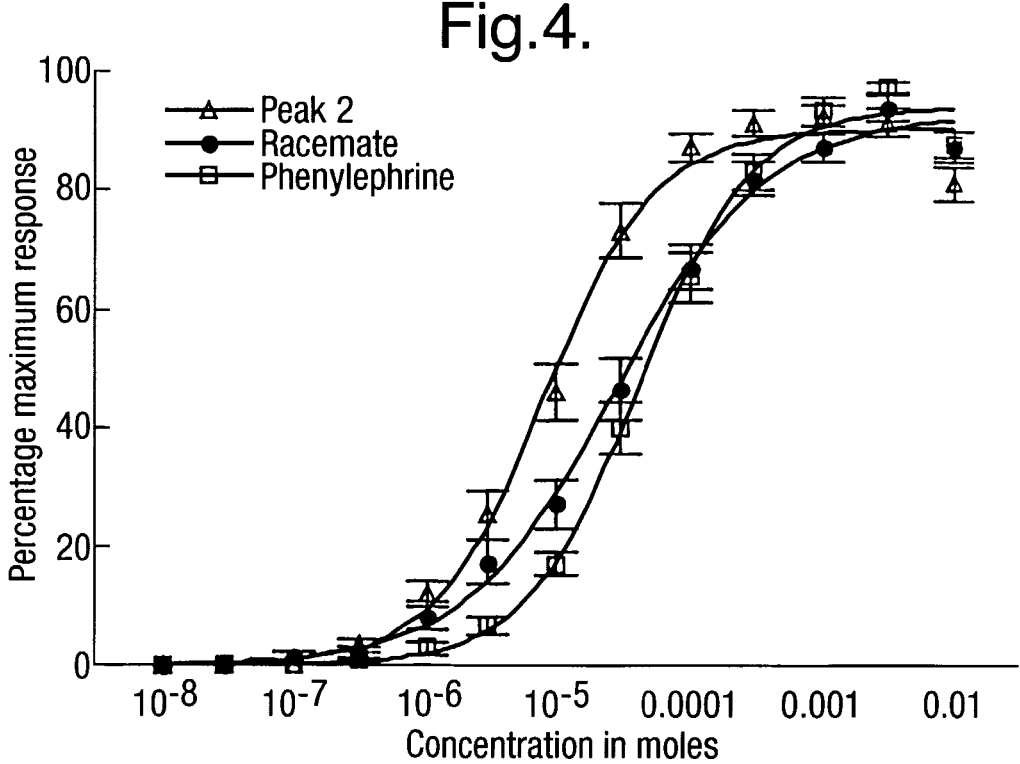

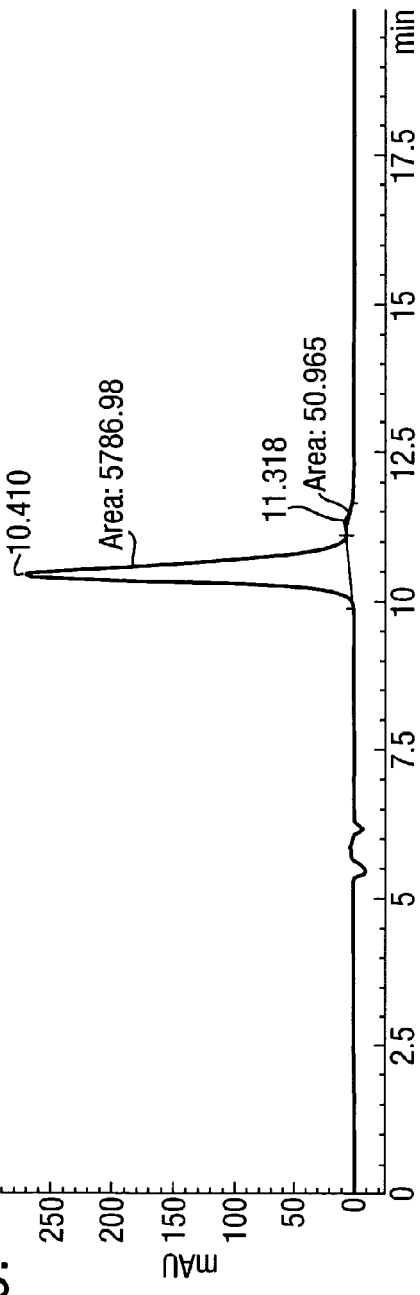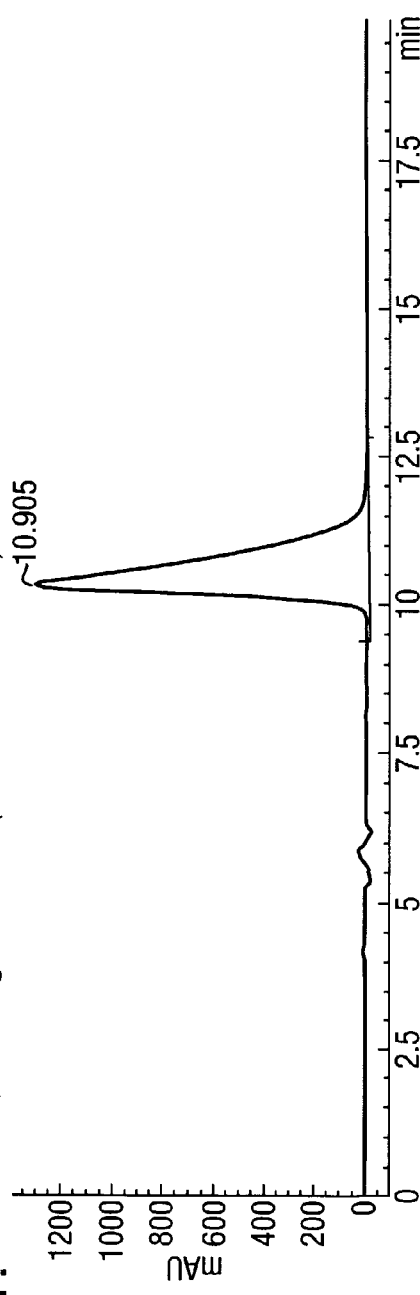

TREATMENT OF FAECAL INCONTINENCE AND OTHER CONDITIONS WITH 1R, 2S-METHOXAMINE

CROSS-REFERENCE TO RELATED APPLICATIONS

This application is a continuation of U.S. application Ser. No. 12/586,973, filed Sep. 30, 2009, in issue, which is a continuation of U.S. application Ser. No. 10/499,873, filed Dec. 27, 2004, now abandoned, which is a United States national stage filing under 35 U.S.C. §371 of international (PCT) application no. PCT/GB2002/005864, filed Dec. 20, 2002, and designating the US, which claims priority to United Kingdom (GB) Application. No. 0130763.6, filed Dec. 21, 2001.

INTRODUCTION

The present invention relates to treatment of faecal incontinence and other conditions.

BACKGROUND OF THE INVENTION

Faecal incontinence affects around 2% of the adult population[1]. It is even more prevalent in the elderly, and it is likely that many people do not seek help for their symptoms. The most common cause of faecal incontinence is damage to the anal sphincter complex during childbirth[2], either through pudendal neuropathy or direct trauma as a result of childbirth. Faecal incontinence may also be seen in the absence of structural injury; in such circumstances, isolated degeneration of the internal anal sphincter (IAS) is the most common cause[3].

Conservative measures for mild symptoms of incontinence includes pads[4], plugs[5], anti-diarrhoeal medications[6] and dietary modification. Some cases will not be controlled with such measures, however. Damage to the external anal sphincter may be amenable to overlapping surgical repair[7] though results of internal sphincter repair have been disappointing[8]. More extensive surgical procedures do exist for more profound damage, including the artificial bowel sphincter[9], sacral nerve stimulation[10] and graciloplasty[11]. These are major interventions and may be either unsuitable or poorly tolerated by many patients.

The use of topical agents for the treatment of faecal incontinence is a different approach to an old problem. WO98/27971 proposes the use of a variety of agents in the treatment of faecal incontinence. Those agents include α-adrenoceptor agonists, nitric oxide synthase inhibitors, prostaglandin $F_{2\alpha}$, dopamine, morphine, β-blockers, and 5-hydroxytryptamine. However, experimental data is given only for phenylephrine, and the nitric oxide synthase inhibitor Nω-nitro-L-arginine.

All clinical research on topical therapies for faecal incontinence has, to date, been focussed on phenylephrine, an α-1 adrenoceptor agonist. (Such agents were previously called α-1 adrenergic agonists.) The use of topical phenylephrine is alleged to produce a dose-dependent rise in resting anal canal pressure of normal human subjects. When applied to the anus of normal human subjects, a gel comprising 10% by weight phenylephrine produced a 33% rise in resting anal pressure that was sustained for a median of 7 hours[12], see also WO98/27971. The use of topical phenylephrine gels was repeated in patients with ultra-sonographically normal anal sphincters, but low resting anal canal pressures and symptoms of incontinence. In this group, however, no significant rise in resting anal pressure was seen with 10% to 20% by weight phenylephrine gels, although increases did achieve statistical significance in those subjects treated with 30% and 40% gels[13]. This data suggests that the internal anal sphincter of patients with incontinence is less sensitive to adrenoceptor agonists than the sphincter in normal subjects. There is data to support this from in vitro studies, too[14].

This fact may also explain why, when the work using phenylephrine was extended to a randomised controlled trial including 36 patients with incontinence and ultrasonographically normal sphincters, no significant overall improvements were seen in incontinence scores, resting anal canal pressure or anodermal blood flow when using 10% phenylephrine gels[15]. By contrast, in a small, randomized controlled trial of patients with faecal leakage after ileoanal pouch construction, 10% phenylephrine gel was found to produce a significantly greater subjective improvement in continence compared to placebo[16].

These results show that, to be effective for treatment of faecal incontinence, it will be necessary for topical phenylephrine preparations to contain high concentrations of phenylephrine, of the order of 30-40% by weight. At these levels, perianal burning has been reported[15]. For that reason alone, such preparations are not suitable for use in treatment.

Phenylephrine, which acts on α-adrenergic receptors of the vascular musculature, has hypertensive effects, also known as anti-hypotensive or pressor effects, and has been used systemically in the treatment of hypotensive states. Another concern with the topical use of phenylephrine for treatment of faecal incontinence is that, at the high doses required to treat faecal incontinence effectively, i.e. using topical preparations containing 30 to 40% by weight of phenylephrine, the topically administered α-adrenoceptor agonist could act systemically on the vasculature, affecting blood pressure and/or pulse rate.

These concerns regarding the topical use of high doses of an α-adrenoceptor agonist in the treatment of faecal incontinence are supported by the facts that cardiovascular side effects are seen when phenylephrine is applied topically in ophthalmology[17], and that local irritation is also observed[18]. These concerns also apply to other α-adrenoceptor agonists that act on the α-adrenergic receptors of the vasculature, which agonists have similar vasoconstrictor and hypertensive properties as phenylephrine, and which may be used for the same indications as phenylephrine i.e. as a pressor agent and as a vasoconstrictor agent. Methoxamine (2-amino-1-(2,5-dimethoxyphenyl)-1-propanol) is an example of such an α-adrenoceptor agonist.

Methoxamine has two chiral centres and hence has four stereoisomers. The methoxamine currently used clinically as a pressor agent and as a vasoconstrictor agent, is in the form of a mixture of isomers.

Fujita and Hiyama[19] have described what is said to be a method for the erythro-directed reduction of α-substituted alkanones by means of hydrosilanes in acidic media. One of the compounds produced is said to be (1R,2S)-2-amino-1-(2,5-dimethoxyphenyl)-1-propanol, which is also called L-erythro-methoxamine by Fujita and Hiyama. However, Fujita and Hiyama did not identify the putative 1R,2S-methoxamine isomer (or any other isomer they produced) definitively i.e. by single crystal X-ray diffractometry, nor did they make any investigations as to the biological activity of the putative 1R,2S-methoxamine isomer (or any other isomer they produced). Furthermore, although the synthetic method described is suitable for producing small amounts, of about 1 g, of the product, we found that the method did not yield the alleged 1R,2S-isomer selectively when scaled up to produce amounts larger than about 1 g, for example, for example, to produce about 30 g to 50 g of the isomer.

The method of Fujita and Hiyama involves the reduction of an α-aminoketone to an alcohol. The authors point out that over-reduction to the hydrocarbon was commonly observed in previously described methods for reducing an α-aminoketone.

The authors state that, using their method, formation of the hydrocarbon was not detected by common analytical methods. They state that, in addition, highly erythro selective reduction was recognized. Selectivity of >99% said to be observed.

Although we obtained similar results when producing the alleged 1R,2S-isomer of methoxamine (L-erythro-methoxaine) on a small scale, of about 1 g, on scaling up to 30 g to 50 g batches we found that, contrary to the findings of Fujita and Hiyama, over-reduction did occur, with more than 60% to 70% of the product being the hydrocarbon instead of the desired alcohol. Furthermore, the process was not erythro selective. Substantial amounts of the threo isomer were formed.

Fujita and Huiyama use both the "R,S" nomenclature and the "erythro/threo" nomenclature when referring to their method and the isomers produced. As the Cahn-Ingold-Prelong "R,S" nomenclature is generally accepted as defining an isomer unambiguously, the "R,S" terminology rather than the "erythro/threo" terminology is used herein to define methoxamine isomers.

SUMMARY OF THE INVENTION

We have synthesised 1R,2S-methoxamine, also known as L-erythro-methoxamine, and have confirmed by nuclear magnetic resonance (NMR) spectroscopy and single crystal X-ray diffractometry that the isomer has the following structure:

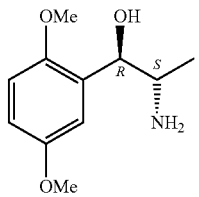

The present invention provides 1R,2S-methoxamine for use as a medicament.

The present invention provides 1R,2S-methoxamine for use as an α-adrenoceptor agonist.

The present invention provides 1R,2S-methoxamine for use in increasing the tone of smooth muscle of the gastrointestinal tract, and for use in treating a disturbance or disorder resulting from loss of tone of smooth muscle of the gastrointestinal tract.

The present invention also provides 1R,2S-methoxamine for use in increasing the tone of a sphincter of the gastrointestinal tract, and for use in treating a disturbance or disorder resulting from loss of tone of a sphincter of the gastrointestinal tract. For example, the present invention provides 1R,2S-methoxamine for use in increasing the tone of the pyloric sphincter, and for use in treating of gastrogenous diarrhoea, and for use in increasing the tone of the gastroesophageal sphincter, and for use in treating oesophageal reflux and Barrett's disease.

The present invention provides 1R,2S-methoxamine for use in increasing anal sphincter tone, and for use in treating faecal incontinence.

The present invention also provides 1R,2S-methoxamine for use in the prevention or treatment of disturbances or disorders of cardiac function, for example, disturbances or disorders of cardiac rhythm.

The present invention also provides 1R,2S-methoxamine for use for use as a vasoconstrictor agent. The present invention also provides 1R,2S-methoxamine for use for use as a nasal decongestant and for use as an ophthalmological vasoconstrictor, and as a mydriatic agent for dilating the pupil of the eye.

The present invention also provides 1R,2S-methoxamine for use as a hypertensive (pressor) agent, for example, in the prevention or treatment of hypotension, for example, for maintaining blood pressure during and/or after anaesthesia.

The invention further provides the use of 1R,2S-methoxamine for the manufacture of medicament for any of the above uses.

The invention also provides a method of treating a mammal in need of treatment with an α-adrenoceptor agonist, which comprises administering a therapeutically effective amount of 1R,2S-methoxamine to the mammal.

The present invention provides a method of increasing the tone of smooth muscle of the gastrointestinal tract of a mammal, which comprises administering a therapeutically effective amount of 1R,2S-methoxamine to the mammal.

The present invention provides a method of treating a disturbance or disorder resulting from loss of tone of smooth muscle of the gastrointestinal tract, which comprises administering a therapeutically effective amount of 1R,2S-methoxamine to a mammal in need of said treatment.

The present invention provides a method of increasing the tone of a sphincter of the gastrointestinal tract of a mammal, for example, the pyloric sphincter or an anal sphincter, which comprises administering a therapeutically effective amount of 1R,2S-methoxamine to the mammal.

The present invention provides a method of treating a disturbance or disorder resulting from loss of tone of a sphincter of the gastrointestinal tract, which comprises administering a therapeutically effective amount of 1R,2S-methoxamine to a mammal in need of said treatment. Such disorders include gastrogenous diarrhoea and faecal incontinence.

The present invention also provides a method for the prevention or treatment of disturbances or disorders of cardiac function in a mammal, which comprises administering a therapeutically effective amount of 1R,2S-methoxamine to a mammal in need of said prevention or treatment. Such disturbances and disorders include disturbances or disorders of cardiac rhythm.

The invention also provides a method treating a mammal in need of treatment with a vasoconstrictor agent, which comprises administering a therapeutically effective amount of 1R,2S-methoxamine to a mammal in need of such treatment. Such treatment may be of nasal congestion, of redness of the eye, or may be to dilate the pupil of the eye.

The invention also provides a method of treating or preventing hypotension, which comprises administering a therapeutically effective amount of 1R,2S-methoxamine to a mammal in need of such treatment, for example, to maintain blood pressure during anaesthesia.

The 1R,2S-methoxamine may be in the form of the free base or a salt thereof. For use in treatment, the salt should be a physiologically tolerable salt.

The present invention also provides a pharmaceutical composition comprising 1R,2S-methoxamine or a physiologically tolerable salt thereof in admixture or conjunction with a pharmaceutically suitable carrier.

The present invention also provides a process suitable for the production of 1R,2S-methoxamine, which comprises adding trifluoroacetic acid dropwise to a solution comprising dimethylphenylsilane and (S)-amino-1-(2,5-dimethoxy-phenyl)-1-propanone, the amino group of which is protected, for example, with an alkoxy- or aryloxycarbonyl group, for example, a methoxycarbonyl group, and removing the protecting group from the resulting amino-protected (1R,2S)-2-amino-1-(2,5-dimethoxy-phenyl)-1-propanol. The solvent for the solution of the silane and the propanone is, in particular, a chlorinated hydrocarbon, for example, dichloromethane. The reduction of the propanone using dimethylphenylsilane should be carried out with cooling. The reaction is generally carried out with ice-cooling, for example, at a temperature in the region of 0° C. This process enables production of 1R,2S-methoxamine on a scale greater than 1 g, for example, on a scale of 30 to 50 g or greater.

The resulting 1R,2S-methoxamine may be converted into a salt thereof, for example, a salt with an acid, for example, a salt as described above, for example, by reaction with an acid.

The present invention also provides a method for isolating the 1R,2S-isomer of methoxamine from a mixture of methoxamine isomers, which comprises subjecting the mixture of isomers to high pressure liquid chromatography using a chromatography medium that comprises β-cyclodextrin R,S-hydroxypropyl ether, bonded to silica gel, preferably followed by reversed phase chromatography using a chromatography medium comprising a vinyl alcohol copolymer base derivatized by the introduction of octadecyl (C18) groups on the hydroxyl groups of the vinyl alcohol copolymers.

BRIEF DESCRIPTION OF THE FIGURES

FIGS. 2 to 5 show dose/response curves for internal anal sphincter muscle tested in vitro. In FIGS. 2 and 4 phenylephrine was used as the control. The four methoxamine isomers were separated using liquid chromatography under the conditions set out in Example 3. They are named in terms of the peaks 1 to 4 as separated by chromatography.

FIG. 2 shows the dose response curves using methoxamine racemate (black circles) and phenylephrine (open squares).

FIG. 3 shows the dose response curves using the four methoxamine isomers, peak 1 (black circles), peak 2 (open squares), peak 3 (open triangles) and peak 4 (X), as obtained using liquid chromatography under the conditions set out in Example 3.

FIG. 4 shows the dose response curves using the methoxamine racemate (black circles), peak 2 (open triangles) and phenylephrine (open squares).

FIG. 5 shows the dose response curves using 1R,2S-methoxamine synthesised according to Example 4, denoted peak 2 (synthetic) (open squares) and 1R,2S-methoxamine obtained by chromatographic separation according to Example 3 and denoted peak 2 (separated) (black circles).

FIGS. 6 to 11 show the chromatograms of methoxamine racemate and the four isomers as obtained using liquid chromatography under the conditions set out in Example 3.

FIG. 6 is the chromatogram of the racemate, showing four peaks (WWD1 A, Wavelength=225 nM (Sample\01-16-8.D).

FIG. 7 is a chromatogram of methoxamine racemate showing where cuts were made to collect separated peaks 1 to 4.

FIG. 8 is a chromatogram showing the purity of peak 3 (WWD1 A, Wavelength=225 nM (Sample\0116P3-5.D).

FIG. 9 is a chromatogram showing the purity of peak 4 (WWD1 A, Wavelength=225 nM (Sample\0116P4-1.D).

FIG. 10 is a chromatogram showing the purity of peak 1 (WWD1 A, Wavelength=225 nM (Sample\0116P1-4.D).

FIG. 11 is a chromatogram showing the purity of peak 2 (WWD1 A, Wavelength=225 nM (Sample\0116P2-4.D).

DETAILED DESCRIPTION OF THE INVENTION

Figure 1:
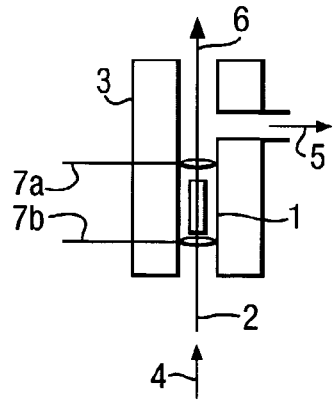
FIG. 1 shows a superfusion organ bath in which strips of pig internal anal sphincter muscle were tested using methoxamine racemate and the four individual isomers.

The present invention relates to 1R,2S-methoxamine and its therapeutic uses, for example, as an α-adrenoceptor agonist.

We have found that 1R,2S-methoxamine is effective at low doses in inducing contraction of internal anal sphincter muscle in vitro and when applied topically in vivo, and that the effect in vivo is not accompanied by an increase in blood pressure.

We found that 1R,2S-methoxamine is at least four times more potent than phenylephrine at inducing contraction of internal anal sphincter muscle in vitro. We have also found, in trials on pigs in vivo, that a dose of 0.5 ml of a gel containing 1% by weight 1R,2S-methoxamine and even a dose as small as 0.5 ml of a gel containing 0.3% by weight 1R,2S-methoxamine i.e. doses of 5 mg and 1.5 mg of 1R,2S-methoxamine, respectively, when applied topically increase internal anal sphincter pressure without any effect on blood pressure.

These findings are highly significant because topical administration of 1R,2S-methoxamine results in increases in anal muscle tone and in anal canal pressure quantitatively similar to those seen with phenylephrine when applied topically but at only a fraction of the concentration and of the dose of phenylephrine required, and without increase in blood pressure.

Methoxamine in the form of a mixture of isomers has been described previously as acting as an α-adrenoceptor agonist at the α-adrenergic receptors of the vascular musculature. Without being limited by the following, we consider that the effects of 1R,2S-methoxamine observed on anal muscle tone in vitro and on anal sphincter tone in vivo are the result of 1R,2S-methoxamine acting directly on the anal sphincter, via the α-adrenergic receptors in the sphincter muscles themselves, rather than acting indirectly via the vascular musculature of the blood vessels supplying the muscles. α-Adrenergic receptors occur throughout the gastrointestinal tract, in the smooth musculature of the tract itself and in the various sphincters of the tract, including the internal anal sphincter, the gastroesophageal sphincter, the pyloric sphincter, the sphincter of Oddi, and the ileocolic sphincter. Reduction of tone in smooth muscle of the gastrointestinal (GI) tract or of any of the GI tract sphincters can lead to disturbances in the normal functioning of the tract, or to clinical disorders. For example, reduction of tone of anal sphincters can result in faecal incontinence; reduction in tone of the pyloric sphincter may be a cause of gastrogenous diarrhoea.

1R,2S-Methoxamine may be used to increase the tone of smooth muscle of the gastrointestinal tract, and to treat a disturbance or disorder resulting from loss of tone of smooth muscle of the gastrointestinal tract. 1,2S-Methoxamine may also be used to increase the tone of a sphincter of the gastrointestinal tract, and to treat a disturbance or disorder resulting from loss of tone of a sphincter of the gastrointestinal tract.

For example, 1R,2S-methoxamine may be used to increase anal sphincter tone, and to treat faecal incontinence. Topical administration of 1R,2S-methoxamine enables effective treatment of faecal incontinence without significant systemic side-effects, in particular without adverse cardiovascular effects, for example, on blood pressure, and without local irritation. 1R,2S-Methoxamine may be used to increase the tone of the pyloric sphincter, and to treat gastrogenous diarrhoea.

α-Adrenergic receptors are also present in cardiac muscle. Disturbances of cardiac function, for example, disturbances of cardiac rhythm, may be prevented or treated by the use of 1S,2S-methoxamine, generally administered systemically.

Methoxamine in the form of a mixture of isomers is currently used as a pressor agent, also known as a hypertensive or anti-hypotensive agent, and as a vasoconstrictor agent. It is considered that the pressor and vasoconstrictor effects are achieved by the action of the methoxamine on the α-adrenoceptor receptors of the vascular musculature. 1R,2S-methoxamine may be used in the treatment of any indication for which an α-adrenergic agonist may be used, in particular, as an α-adrenoceptor agonist acting on the α-adrenergic receptors of vascular musculature, for example, for any of the indications for which methoxamine, in the form of a mixture of isomers, or phenylephrine is used or has been used. In particular, 1R,2S-methoxamine may be used as a pressor agent or as a vasoconstrictor agent.

The subject to be treated according to the present invention is a mammal. The mammal is generally a human but may be a commercially reared animal or a companion animal.

For use in treatment 1R,2S-methoxamine may be used as such, that is to say, in the form of the free base, or in the form of a physiologically tolerable salt thereof. Unless specified otherwise, the term "1R,2S-methoxamine" as used below includes both the free base and physiologically tolerable salts thereof. When amounts or percentages of 1R,2S-methoxamine or a salt thereof are given, the amount or concentration of a salt is preferably calculated on the basis of the free base 1R,2S-methoxamine.

Salts of 1R,2S-methoxamine are, for example, salts with acids, including acid addition salts. Examples of salts are those with hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid ethanesulphonic acid, p-toluenesulphonic acid, benzenesulphonic acid, isethionic or camphoric acid.

1R,2S-methoxamine may be administered systemically or non-systemically, generally in the form of a pharmaceutical composition of the present invention. The route of administration of 1R,2S-methoxamine, the appropriate pharmaceutical compositions and also the preferred dose depend on the intended use.

The invention also provides a method suitable for the production of 1R,2S-methoxamine on a scale that is suitable for pharmaceutical use, for example, in amounts greater than about 1 g, for example, of about 30 g to 50 g or more. The method is described above and in more detail below. The method proposed previously by Fujita et al only works on a small scale, about up to 1 g. Such a scale is too small even for the production of a substance for clinical trials. Accordingly, none of the uses described herein was possible before the development of the process of the present invention.

The present invention provides a pharmaceutical composition comprising 1R,2S-methoxamine or a physiologically tolerable salt thereof as active ingredient, in admixture or conjunction with a pharmaceutically suitable carrier.

A pharmaceutical composition of the present invention may be in a form suitable to achieve a systemic or local effect.

The term "systemic" is used herein to denote "pertaining to or affecting the body as a whole". The term "local" is used to denote "restricted to or pertaining to one spot or part; not general". The term "topical" means "pertains to a particular surface area". A pharmaceutical composition suitable for topical administration to a particular surface area, for example, of the skin, generally provides an effect that is local rather than systemic. However, some topical formulations may be designed for primarily systemic administration of the active ingredient. Unless specified otherwise, the term "topical", for example, as in topical administration or topical pharmaceutical composition, is used herein to denote "pertaining to a particular surface area and having a local effect".

Pharmaceutical compositions of the present invention include compositions suitable for administration of 1R,2S-methoxamine by injection or infusion; for subcutaneous administration; transdermal administration; oral, including sub-lingual, administration; rectal administration; and topical administration, for example, administration to the skin, to the surface of the eye or to the nasal mucosa.

Suitable pharmaceutical compositions for oral and sublingual administration are known. Tablets and capsules are widely used for oral administration, with other formulations, for example, pills, granulates, dragees and wafers being less common. Delayed or targeted release formulations may be used, for example, formulations that target release to a pre-determined part of the GI tract, for example, time-delayed release or pH dependent formulations, for example, formulations that target release to the stomach, duodenum or lower GI tract, for example, the colon. For example, formulations that are designed to release the active ingredient at the ambient pH of the colon may be used, as may colon-targeting formulations that comprise a coating that is susceptible to degradation by colonic bacteria. Formulations may be targeted to other parts of the gastrointestinal tract, for example, to the stomach or duodenum. Liquid preparations, for example, syrups, or thickened liquids, for example, thickened gels, or slurrys, may be used for oral administration.

Pharmaceutical compositions suitable for rectal administration include suppositories, gelatin rectal capsules and enema solutions.

Pharmaceutical compositions suitable for administration to the nasal mucosa are, for example, drops, sprays and aerosols. Compositions for administration to the surface of the eye are, for example, drops, creams and ointments.

A pharmaceutical composition of the invention may be, for example, in a form suitable for topical administration to the skin, for example, a gel, cream, ointment, paste, foam or adhesive patch.

A pharmaceutical composition may be for subcutaneous administration. Some compositions, for example, subcutaneous depot preparations and adhesive patches may provide delayed or sustained release.

Pharmaceutical compositions as described above may also comprise one or more further active ingredients in addition to 1R,2S-methoxamine. For example, compositions for topical administration to the anal region for the treatment of faecal incontinence may comprises any of the pharmaceutically active ingredients typically present in compositions for topical administration to the anal region, for example, a steroid, which may act to reduce irritation, and/or a local anaesthetic agent. A pharmaceutical composition for topical administration to the skin in the anal region may also comprise any one or agents selected from skin penetration enhancing agents, skin hydrating agents, and skin softening agents. A topical composition for administration to the skin may be presented, for example, in a tube, a container with a pump, or in an aerosol can.

A pharmaceutical preparation of the present invention for topical administration to the skin, for example, a gel, cream or ointment, especially a composition intended for use in the treatment of faecal incontinence, generally comprises not more than 10% by weight of 1R,2S-methoxamine and usually less than 10%, for example up to and including 8%, for example, up to and including 5%, for example, up to and including 4%, 3%, 2% or 1% 1R,2S-methoxamine. Preparations comprising 1% or less by weight of methoxamine may be used, for example, 0.8% or less, for example, 0.5% or less, for example, 0.3% or less, for example, 0.1% by weight 1R,2S-methoxamine. A composition may comprise, for example, from 0.1% to 5% by weight, for example, from 0.3 to 3% by weight of 1R,2S-methoxamine. The preparation may be administered one or more times per day, for example, two or three times per day, even more often, for example, four or five times per day. A unit dose of a topical preparation is typically about 1 ml of a gel, ointment or cream, for example, comprising an amount of 1R,2S-methoxamine are described above. The dose of 1R,2S-methoxamine administered per application may be calculated from the volume of composition administered and the concentration of 1R,2S-methoxamine in the composition. For example, 1 ml of a 1% by weight 1R,2S-methoxamine gel provides a dose of 10 mg of a dose of 1R,2S-methoxamine.

A pharmaceutical composition of the present invention may be in unit dosage form. Examples of unit dosage forms for systemic administration are described above. For oral or rectal administration unit dosage forms include, for example, tablets, capsules and suppositories, for administration by injection or infusion unit dosage forms include, for example, vials and ampoules. Unit dosage forms for topical administration to the skin include blister packs or sachets, each blister or sachet containing a unit dose of, for example, a gel, cream or ointment, for example, as described above. A metered dosing device may be provided, for example, a pump device, for dosing a predetermined volume of a topical composition, for example, a cream, ointment or gel. For use as mydriatic agent for dilating the pupil of the eye, single drop unit doses are provided. A preparation may provide sustained release, for a depot preparation or an adhesive patch.

Pharmaceutical compositions of the various types described above and other compositions suitable for the routes of administration described above are known, as are formulations for such compositions and methods for their preparation. The literature of the art includes handbooks, for example, Remington's Pharmaceutical Sciences by E W Martin. Reviews and literature articles describe both standard and more sophisticated formulations and devices, for example, various types of adhesive patches.

As indicated above, the route of administration of 1R,2S-methoxamine, the appropriate pharmaceutical compositions, and the preferred dose depend on the intended use. In clinical treatment, it is generally preferable to use the lowest dose that achieves the desired effect. 1R,2S-methoxamine has at least four times the potency of methoxamine racemate, that is to say, an equimolar mixture of all four isomers. Accordingly when used for an indication for which methoxamine racemate has previously been used, the dose of 1R,2S-methoxamine should generally be reduced, for example, to at least half of the previous dose, for example, to about one quarter. Even lower doses may be used.

For use as a pressor agent, for the treatment of hypertension, 1R,2S-methoxamine is generally administered systemically. For example, when used to maintain blood pressure during anaesthesia, 1R,2S-methoxamine is administered by injection or infusion, generally by intravenous injection or infusion.

The recommended dose of a solution containing 20 mg/ml methoxamine in the form of a mixture of isomers available commercially for use as a pressor agent to maintain blood pressure during anaesthesia is from 0.15 to 0.25 ml when administered intravenously, and 1 ml when administered intramuscularly, i.e. the recommended dose is from 3 to 5 mg when administered intravenously and about 20 mg when administered intramuscularly. The dose of 1R,2S-methoxamine for use as a pressor agent to maintain blood pressure during anaesthesia may be, for example, half of that dose or less, for example, one quarter of that dose or less, for example, 1 mg or less when administered intravenously and 5 mg or less when administered intramuscularly.

For use as a nasal decongestant, 1R,2S-methoxamine is generally administered topically to the nasal mucosa, for example, in the form of a drops, a spray or an aerosol.

1R,2S-methoxamine may be used as an ophthalmic vasoconstrictor agent, for example, for the treatment of redness of the eye, for example, caused by an allergic reaction, a dry, dusty or smoky environment, failure to blink correctly, or tiredness. 1R,2S-methoxamine may also be used as a mydriatic agent, for dilation of the pupil of the eye. For ophthalmic use, 1R,2S-methoxamine may be administered topically to the surface of the eye, for example, in the form of drops, a cream or an ointment.

For treatment of faecal incontinence, 1R,2S-methoxamine may be administered topically, for example, in the region of the anus and buttocks. Pharmaceutical compositions suitable for such topical administration include gels, creams, ointments, pastes and foams; liquid compositions, particularly thickened liquids; subcutaneous depot preparations; and transdermal patches.

Topical administration of 1R,2S-methoxamine according to the present invention, that is to say, topical administration having a local effect, has the advantage of reducing the systemic affects of methoxamine, for example, the effects on blood pressure.

It may be advantageous to administer the 1R,2S-methoxamine to the anal region, that is to say, to all or part of the anus, the anal canal, and the area around the anus, which is called the perianal region, for example, to any or all of the anoderm, the anal canal, the internal anal sphincter, and the buttocks.

For example, a cream, ointment, gel or foam may be applied using an applicator or the finger to the anal canal and/or the skin around the anus.

An alternative is to inject 1R,2S-methoxamine directly into the muscle of the anal sphincter or into other tissue in the anal region. A systemic transdermal patch applied to a buttock, in particular near the anal region, will have a local effect in addition to a systemic effect.

When a topical preparation is an ointment, cream, gel or paste in a tube, the instructions for use may recommend an appropriate amount to be used, for example, to squeeze about 2-3 cm of preparation from the tube. A topical preparation may be provided in a container that comprises a pump and metered dosing device to assist correct dosing. In general, from about 0.5 to about 3 ml, for example, about 1 ml, is a suitable volume of a cream, gel or ointment for topical application. However, when applying a topical preparation, especially when using the finger, it is often difficult to administer a precise dose. Use of an applicator may give more precise dosing.

The instructions for use should indicate the recommended site of application, for example, whether the preparation should be applied to the skin around the anus or whether the preparation should also be inserted into the anus.

To treat faecal incontinence effectively, it would be necessary to use phenylephrine at a concentration of 30-40% by weight in a topical preparation, for example a gel, typically at a volume of 1 ml, giving a dose of 400 mg of phenylephrine. The total dose of phenylephrine and the high concentration will give systemic and local side effects, in particular, cardiovascular side effects, for example, an increase in blood pressure, and local skin irritation. In contrast, using 1R,2S-methoxamine, 0.5 ml of gels containing 1% by weight and 0.3% by weight of 1R,2S-methoxamine were found to increase internal anal sphincter pressure without any effect on blood pressure in trials on pigs.

According to the present invention, for treatment of faecal incontinence it is preferable to use a pharmaceutical composition suitable for topical administration, for example, a gel, cream or ointment, that generally comprises not more than 10% by weight of 1R,2S-methoxamine and usually less than 10%, for example up to and including 8%, for example, up to and including 5%, for example, up to and including 4%, 3%, 2% or 1% 1R,2S-methoxamine. Preparations comprising 1% or less by weight of methoxamine may be used, for example, 0.8% or less, for example, 0.5% or less, for example, 0.3% or less, for example, 0.1% by weight 1R,2S-methoxamine. From about 0.5 to about 2 ml, preferably about 1 ml, is a suitable volume of a cream, gel or ointment for topical application.

A composition may be administered one or more times per day, for example, two or three times per day, even more often, for example, four or five times per day. A typical unit dose of a topical preparation is about 1 ml of a gel, ointment or cream, for example, comprising an amount of 1R,2S-methoxamine as described above. The dose of 1R,2S-methoxamine administered per application may be calculated from the volume of composition administered and the concentration of 1R,2S-methoxamine in the composition. For example, 1 ml of a 1% by weight 1R,2S-methoxamine gel provides a dose of 10 mg of a dose of 1R,2S-methoxamine. By way of example, doses in the range of from 0.5 mg to 40 mg may be administered. It will be appreciated that the dose actually administered to the relevant site may be less than the theoretical dose, because of wastage during application.

For use in increasing the tone of smooth muscle of the gastrointestinal tract, and for use in treating a disturbance or disorder resulting from loss of tone of smooth muscle of the gastrointestinal tract, and also for use in increasing the tone of a sphincter of the gastrointestinal tract, and for use in treating a disturbance or disorder resulting from loss of tone of a sphincter of the gastrointestinal tract, 1R,2S-methoxamine is preferably administered topically, for example, using a pharmaceutical composition described above, to avoid undesired systemic side effects. Compositions for suitable delayed or targeted administration may be used. For example, for use in increasing the tone of the gastro-esophageal sphincter, and for use in treating reflux, for example, Barnett's disease, 1R,2S-methoxamine may be administered in the form of a thickened liquid, for example a viscous gel, or a slurry. For use in increasing the tone of the pyloric sphincter, and for use in treating of gastrogenous diarrhoea, 1R,2S-methoxamine may be administered in the form of a thickened liquid, for example a viscous gel, or a slurry, or solid oral composition targeted for release in the stomach.

For use in the prevention or treatment of disturbances or disorders of cardiac function, for example, disturbances or disorders of cardiac rhythm, 1R,2S-methoxamine is administered systemically, especially by injection or infusion, for example, in the form of a appropriate pharmaceutical composition as described above, As a general principle, where a local effect is desired, for example, in the treatment of nasal congestion, in ophthalmological use and in the treatment of faecal incontinence, is desirable to achieve that local effect without systemic effect, for example, without affecting blood pressure. The fact that the 1R,2S isomer has greater activity than any of the other isomers or the racemate itself means that the same pharmacological effect can be achieved at a much lower dosage which reduces the level of undesired side effects.

As regards using 1R,2S-methoxamine systemically, a lower dose can be used to achieve the same effect as obtained with a higher does of methoxamine racemate.

As explained above, we found that only very small amounts of 1R,2S-methoxamine can be produced by the method of Fujita and Hiyama[20], for example, up to about 1 g, such amounts being too small for practical purposes. It is therefore preferable to produce the isomer by the process of the invention, which enables much larger scale production, for example, in at least 30 to 50 g batches.

The process of the present invention comprises adding trifluoroacetic acid dropwise to a solution comprising dimethylphenylsilane and (S)-amino-1-(2,5-dimethoxy-phenyl)-1-propanone, the amino group of which is protected, and removing the protecting group from the resulting amino protected (1R,2S)-2-amino-1-(2,5-dimethoxy-phenyl)-1-propanol. The protecting group may be, for example, an alkoxy- or aryloxycarbonyl group, for example, a methoxycarbonyl or a t-butoxycarbonyl group. It is generally preferable to use a protecting group that, relative to other protecting groups, is small and not bulky, in order to minimise the effect of the protecting group on the stereospecificity of the reaction. A methoxycarbonyl protecting group is generally preferred. The solvent for the solution of the silane and the propanone is, in particular, a chlorinated hydrocarbon, for example, dichloromethane. Dichloromethane has the advantage that it is less toxic than other chlorinated hydrocarbons, for example, chloroform. The reduction of the propanone using dimethylphenylsilane, should be carried out with cooling as heat is generated in the reaction. The reaction is generally carried out with ice-cooling, for example, at a temperature in the region of 0° C., while the trifluoroacetic acid is added, and the resulting reaction mixture is preferably maintained at that temperature, for example, for about one hour.

The reaction may be stopped by adding a base, for example, sodium hydroxide. The product may be purified by crystallisation, if desired. The protecting group is removed from the product to converted it to 1R,2S-methoxamine by reduction, preferably using a base, for example, potassium hydroxide, for example, under reflux conditions, for example, for about 20 hours.

The invention also provides a process for producing (1R, 2S)-2-amino-1-(2,5-dimethoxy-phenyl)-1-propanol, the amino group of which is protected, preferably as described above, which comprises adding trifluoroacetic acid dropwise to a solution comprising dimethylphenylsilane and (S)-amino-1-(2,5-dimethoxy-phenyl)-1-propanone, the amino group of which is protected, preferably as described above. The reagents and reaction conditions are preferably as described above.

(S)-Amino-1-(2,5-dimethoxy-phenyl)-1-propanone, the amino group of which is protected, may be produced from L-alanine by the method described by Fujita and Hiyama[20]. In summary, the method comprises protecting the amine group of L-alanine, converting the carboxy group of the N-protected alanine into an acid chloride in situ followed by reaction with an amine to produce an N-protected (S)-alanine amide, and coupling that compound with a chlorinated 2,5-dimethoxybenzene in the presence of n-butyl lithium or a magnesium-based reagent, for example, a Grignard or Grignard-type reagent to give (S)-amino-1-(2,5-dimethoxy-phenyl)-1-propanone, the amino group of which is protected. In the method described by Fujita and Hiyama the amino protecting group is a methoxycarbonly group, the amine is dimethylamine, the chlorinated 2,5-dimethoxy benzene is bromo-2,5-dimethoxy benzene and the reagent used in the coupling reaction is n-butyl lithium. The reaction scheme is shown below.

Fujita and Hiyama give detailed protocols for the production of the various intermediates in the reaction scheme set out above. However, any of the intermediates in the Fujita and Hiyama reaction scheme may be produced by a different or modified process. For example, it is not necessary to follow those protocols in every detail. The reagents and/or the reaction conditions may be varied. For example, Fujita and Hiyama use 3 equivalents of bromo-2,5-dimethoxy benzene in the coupling step. However, when the process was scaled up from about a 1 g batch size to a 30 g to 50 g batch size it was found that the resulting (S)-methoxycarbonyl)amino]-1-(2,5-dimethoxy-phenyl)-1-propanone was difficult to purify. It has been found that, using instead only 1.5 equivalents of bromo-2,5-dimethoxy benzene and n-butyl lithium, the product was much easier to purify and, surprisingly, there was no loss of yield, up to 98% yield being obtained, calculated on the alanine starting material. Further details are given in the Examples below.

The reagents and reaction conditions may be varied as desired, for example, as described above. For example, a different amino protecting group, for example, a t-butoxycarbonyl group may be used. Instead of dimethylamine, methoxymethylamine may be used. Chloro- or iodo-2,5-diemethoxybenzene may be used instead of iodo-2,5-diemethoxybenzene. However, such variants are likely to result in a reduction in yield and/or a reduction in the stereospecificity of the reaction. It is preferable, therefore, to use the recommended reagents and reaction conditions.

Another method of producing 1R,2S-methoxamine is by chromatographic separation of methoxamine racemate, or any mixture of methoxamine isomers. However, separation and isolation by conventional chromatography is almost impossible. Chiral high pressure liquid chromatography

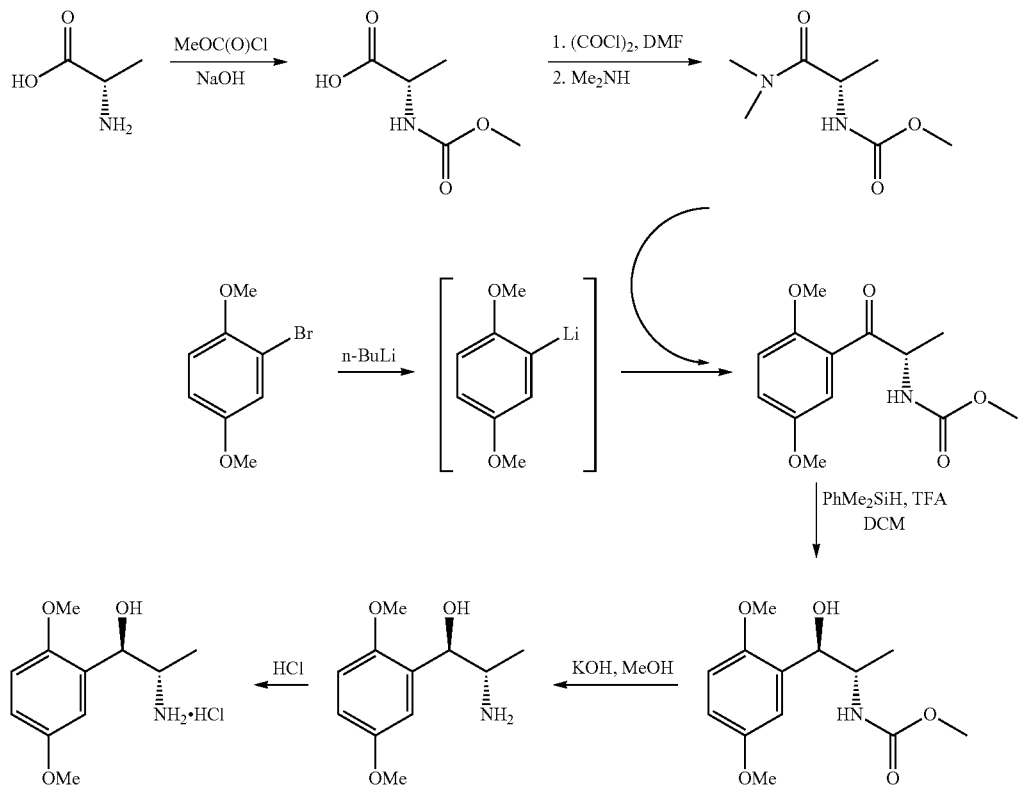

(hplc) is the only practical method, and the use of that technique requires the use of particular modifications.

The chiral chromatography is preferably carried out using chromatographic media designed for separation of isomers. For example, a chromatography medium that comprises β-cyclodextrin R,S-hydroxypropyl ether. Such a medium has the property of forming inclusion complexes. For example, Cyclobond 1 2000 RSP, obtainable from Advanced Separation Technologies, 1 Blake Street, Congelton, Cheshire, England, may be used. That medium is a reversed phase chromatographic medium manufactured by covalently bonding beta cyclodextrin to silica particles. Several of the secondary hydroxyl groups of the cyclodextrin are derivatised with racemic (R,S) hydroxypropyl groups, enabling further hydrogen bonding interactions to take place with the solute. The solute becomes included in the cyclodextrin cavity in reversed phase, and together with the hydroxypropyl side chain interactions, enantio-selectivity takes place. For a review of cyclodextrin chromatography technology, see for example, Ward & Armstrong[21]. A mobile phase comprising 0.1% aqueous triethylamine may be used for chromatography. The pH of the 0.1% aqueous triethylamine may be adjusted to a pH of 4.1, for example, with glacial acetic acid.

The use of Cyclobond 1 RSP enables two of the methoxamine isomers to be isolated from the methoxamine racemate with good purity. To separate the other two isomers it is preferable to subject the eluates containing the two isomers to further chromatography, for example, using a chromatography medium comprising a vinyl alcohol copolymer base derivatized by the introduction of octadecyl (C18) groups on the hydroxyl groups of the vinyl alcohol copolymers. Such a medium is, for example, a C18 column, also available from Advanced Separation Technologies, 1 Blake Street, Congelton, Cheshire, England. A C18 column concentrates the sample from the mobile phase. By washing with water the buffer may be removed. Eluting the column with methanol allows recovery of the purified enantiomers.

The use of Cyclobond 1 RSP followed by C18 gives pure samples of all four isomers. Further details are given in the Examples below. Other analogous chromatographic media may be used instead either or both of Cyclobond 1 RSP and C18, for example, chromatographic media having the same or similar chemical composition and/or the same or similar physico-chemical chromatographic properties.

While suitable for analytical purposes, chromatography is not practical for production of 1R,2S-methoxamine on a scale large enough for practical purposes, for example, for clinical use.

Even using chiral chromatography, it is not possible to correlate the chromatographic fractions unequivocally with isomeric chemical structures. A combination of nmr spectroscopy and single crystal X-ray diffraction analysis was required to enable definitive identification of the 1R,2S isomer of methoxamine, also called 1R,2S-methoxamine.

As stated above, it has now been found that 1R,2S-methoxamine is at least four times more potent at inducing contraction of internal anal sphincter muscle in vitro than phenylephrine. In trials on pigs in vivo, gels containing 1% by weight 1R,2S-methoxamine (L-erythro-methoxamine) and even as little as 0.1% by weight were found to increase internal anal sphincter pressure without any effect on blood pressure. The finding is highly significant because increases in anal canal pressure quantitatively similar to those seen with phenylephrine are achieved at only a fraction of the concentration of phenylephrine required. 1R,2S-Methoxamine is considered to act on the internal anal sphincter via the α-adrenergic receptors in the sphincter muscle.

The following non-limiting Examples illustrate the invention.

Example 1

In Vitro Studies of Methoxamine Isomers on Internal Anal Sphincter Muscle

Methods

Tissue was obtained from female Large White pigs from a local abattoir. Pieces of internal anal sphincter muscle were cut and the tissue was transferred immediately to Krebs solution at 4° C. (120 mM NaCl, 5.9 mM KCl, 15.4 mM $Na_2HCO_3$, 1.2 mM $NaH_2PO_4$, 2.5 mM $CaCl_2$, 1.2 mM $MgCl_2$, 11.5 mM glucose, equilibrated with 97% oxygen and 3% carbon dioxide to maintain the pH at 7.4±0.05). The epithelium of the anal canal was removed along with the submucosa. Strips of the internal anal sphincter (IAS) were cut, each measuring approximately 1×1×7 mm, weighing 2 mg to 8 mg and containing parallel muscle bundles. Fine 5-0 silk ligatures were tied to each end and the strips mounted for isometric tension recording in superfusion organ baths (capacity 0.2 ml)[19] as shown in FIG. 1. The muscle strip 1 is held by a thread 2 to secure it in position within the Perspex jacket 3. The strips were perfused continuously with Krebs solution (37° C.) at a rate of 1 ml/min introduced via an inflow 4 and exiting via an overflow 5. This apparatus allows six strips to be studied simultaneously. The strips were initially loaded with 1 g tension and allowed to equilibrate for at least 90 minutes. Tension was measured by Pioden dynamometer UF1 transducer (Pioden Controls, Canterbury, UK) involving a tension transducer 6 and ring electrodes 7 and 7a, and recorded both on a six channel Tekman 900 pen recorder (Tekman Electronics, Learnington Spa, UK) and using Chart v3.6 and MacLab Data Acquisition System (AD Instruments, Australia).

Phenylephrine (Sigma Chemical Co., Poole, UK), methoxamine racemate and the four methoxamine isomers were dissolved in Krebs solution and tested for their effect on IAS tone. Methoxamine racemate, that is to say, an equimolar mixture of the four isomers, was produced by Prosyth Limited, Acton, Sudbury, Suffolk. The four isomers (called peaks 1 to 4), were separated as described in Example 3. Peak 2 is 1R,2S-methoxamine. The 1R,2S isomer was also synthesised as described in Example 4. It has been confirmed by crystallography that peak 2 is 1R,2S-methoxamine.

IAS strips developed intrinsic tone during the equilibrium period. After equilibration increasing concentrations of each of the test compounds were added for 20 second periods, with intervening washout periods of at least ten minutes, until the tone had returned to baseline.

Results are expressed as mean (standard error of the mean) and the number of surgical specimens from which these strips were derived. A maximum of six strips were used from each pig for each test compound.

Test compound-induced increases in tone were calculated by taking the peak tone after application of the test compound and subtracting this from basal tone. This figure was then expressed as a percentage of maximal increase in tone seen across the dose range used ($10^{-2}$M to $10^{-8}$M). All analysis was performed using Chart v3.6 software.

$EC_{50}$ values were calculated by plotting concentration-response curves for each muscle strip. The dose causing 50% of maximal contraction was calculated by linear regression. $EC_{50}$ values for different drugs were compared using a two-tailed t-test, assuming unequal variance and with p<0.05 considered significant.

Results

Methoxamine Racemate and Phenylephrine

Figure 2:
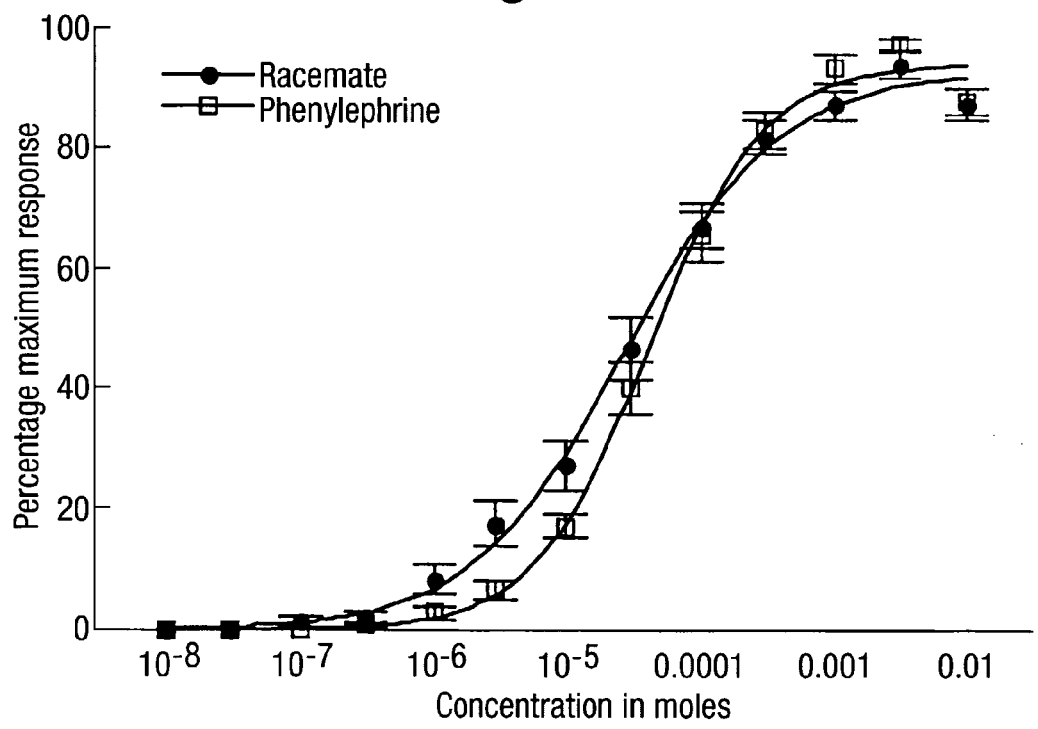

Both methoxamine racemate and phenylephrine caused a dose-dependent contraction of smooth muscle strips from the IAS. $EC_{50}$ values for methoxamine racemate and phenylephrine did not differ significantly ($5.8\times10^{-8}$M vs $7.5\times10^{-5}$M; p=0.44). Concentration-response curves are shown in FIG. 2. n=24(4)

Methoxamine Stereoisomers

All isomers (peaks 1 to 4) caused dose-dependent contraction of smooth muscle from the IAS. $EC_{50}$ values are shown in Table 1.

TABLE 1

| Test compound | Racemate or isomer | $EC_{50}$ value µM (±SE) |
|---|---|---|
| Phenylephrine | Racemate | 74.7 (±16.5) |
| Methoxamine | Racemate | 58.3 (±13.4) |
|  | Peak 1: | 317 (±4.06) |
|  | Peak 2: 1R,2S | 17.6 (±3.71) |
|  | Peak 3: | 165 (±12.1) |
|  | Peak 4: | 483 (±80.6) |

Peak 2, the 1R,2S isomer, was significantly more potent than peaks 1, 3 and 4 (p<0.01). Concentration-response curves for the four isomers are shown in FIG. 3. Peak 2, the 1R,2S isomer, was also significantly more potent than methoxamine racemate and phenylephrine (p<0.01), as shown in the concentration-response curves of FIG. 4.

Chemically Synthesised 1R,2S Methoxamine (Peak 2)

Figure 5:
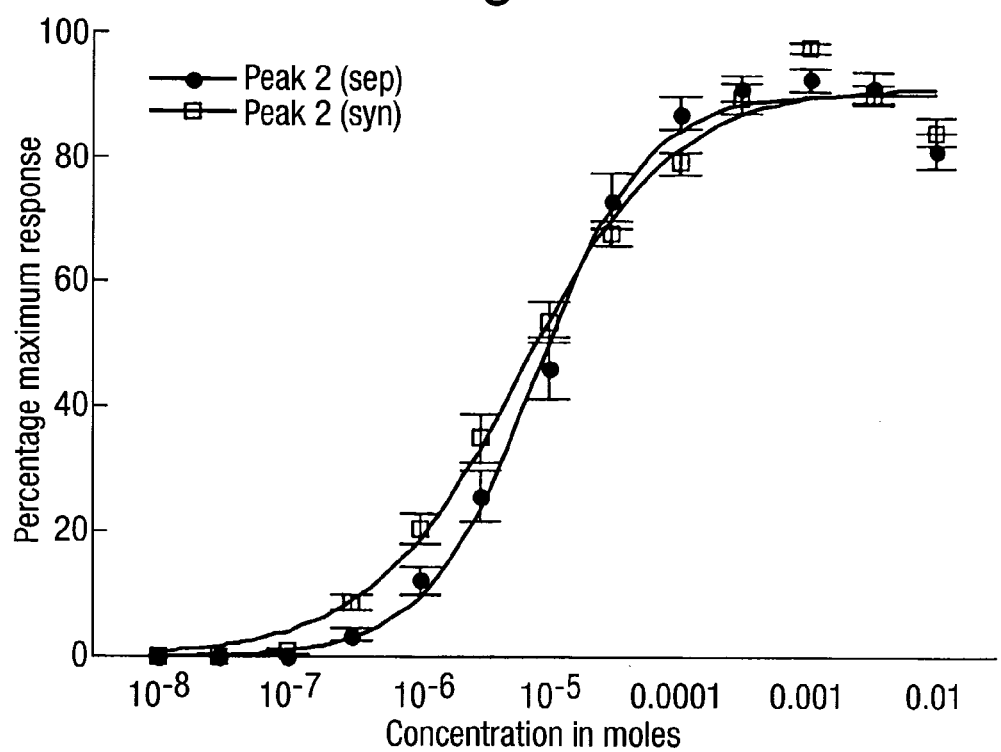

1R,2S methoxamine produced by chemical synthesis as described in Example 4, also caused dose dependent contraction of internal anal sphincter strips. $EC_{50}$ was 10.5 (±1.97) µM. The $EC_{50}$ did not differ significantly from that of peak 2, which is the same isomer obtained by chromatographic separation from the racemate (p=0.10), see FIG. 5. The chemically synthesised 1R,2S isomer was also significantly more potent than methoxamine racemate (p<0.01), phenylephrine (p<0.001), and peaks 1, 3 and 4, see FIGS. 3 and 4.

Example 2

Chromatographic Separation of Methoxamine Isomers

Analytical Purification

Figure 6:
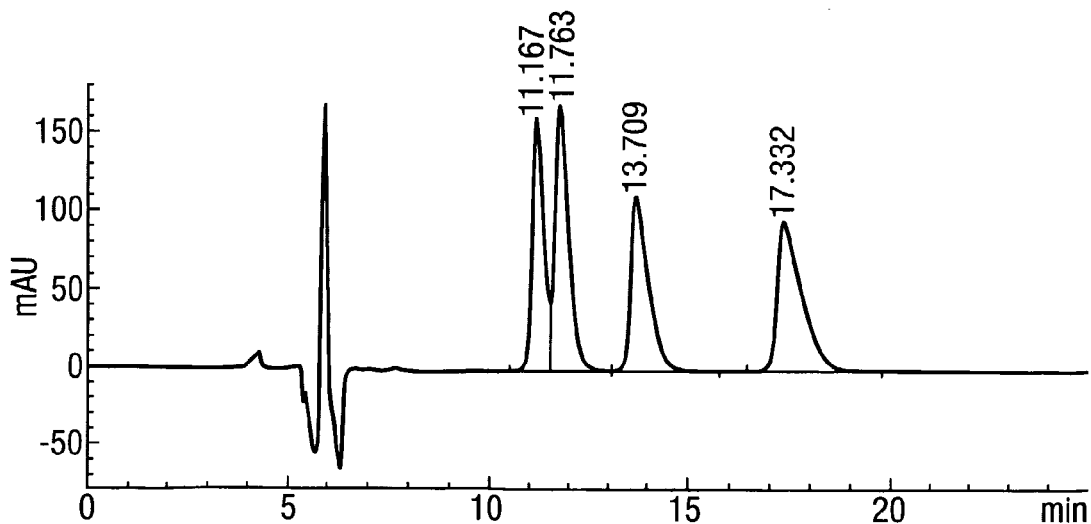

Analytical resolution of a sample of methoxamine racemate obtained from Prosynth Limited, see Example 2, into the four individual enantiomers was carried out under the following chromatographic conditions:

A cyclobond 1 2000 RSP (Advanced Separation Technologies Ltd (Astec) 37 Leslie Court, P.O. Box 297 Whippany, N.J. 07981 USA, was conditioned with mobile phase 5/95; v/v; acetonitrile/0.1% triethylamine acetate, pH 4.1, until a stable baseline was achieved. A sample of methoxamine racemate (1 mg/ml) was prepared in methanol. Ten microliters of the prepared sample were injected into the column, which was operated at a flow rate of 0.6 ml/minute. A UV detector with the wavelength set at 254 nm monitored the column effluent. Four peaks were observed, see FIG. 6. When the column effluent was monitored with a laser polarimeter it was observed that the first two peaks were diastereomers, which means that peaks 1 and 3 and peaks 2 and 4 are enantiomer pairs.

Preparative Purification

To purify 100 mg of each enantiomer the chiral stationary phase was run first and peaks 1 and 2 collected. As diastereoisomers these two peaks were further purified (polished) on an Astec C18 column. In the same run on the RSP column pure peak 3 and pure peak 4 were collected. Since both the C18 run to resolve peaks 1 and 2, and the Cyclobond 1 2000 RSP run contain a non-volatile buffer, a method for adsorbing the resolved methoxamine enantiomers onto a C18 stationary phase was developed. The C18 column concentrates the sample from the mobile phase, and by washing with water, buffer is removed. Finally, eluting the C18 column with methanol allows recovery of the purified enantiomers.

Preparative Purification Method

1. Preparation of triethylamine acetate: a 0.1% aqueous solution of HPLC grade triethylamine was stirred and the pH adjusted to 4.1 with reagent grade glacial acetic acid.

Figure 7:
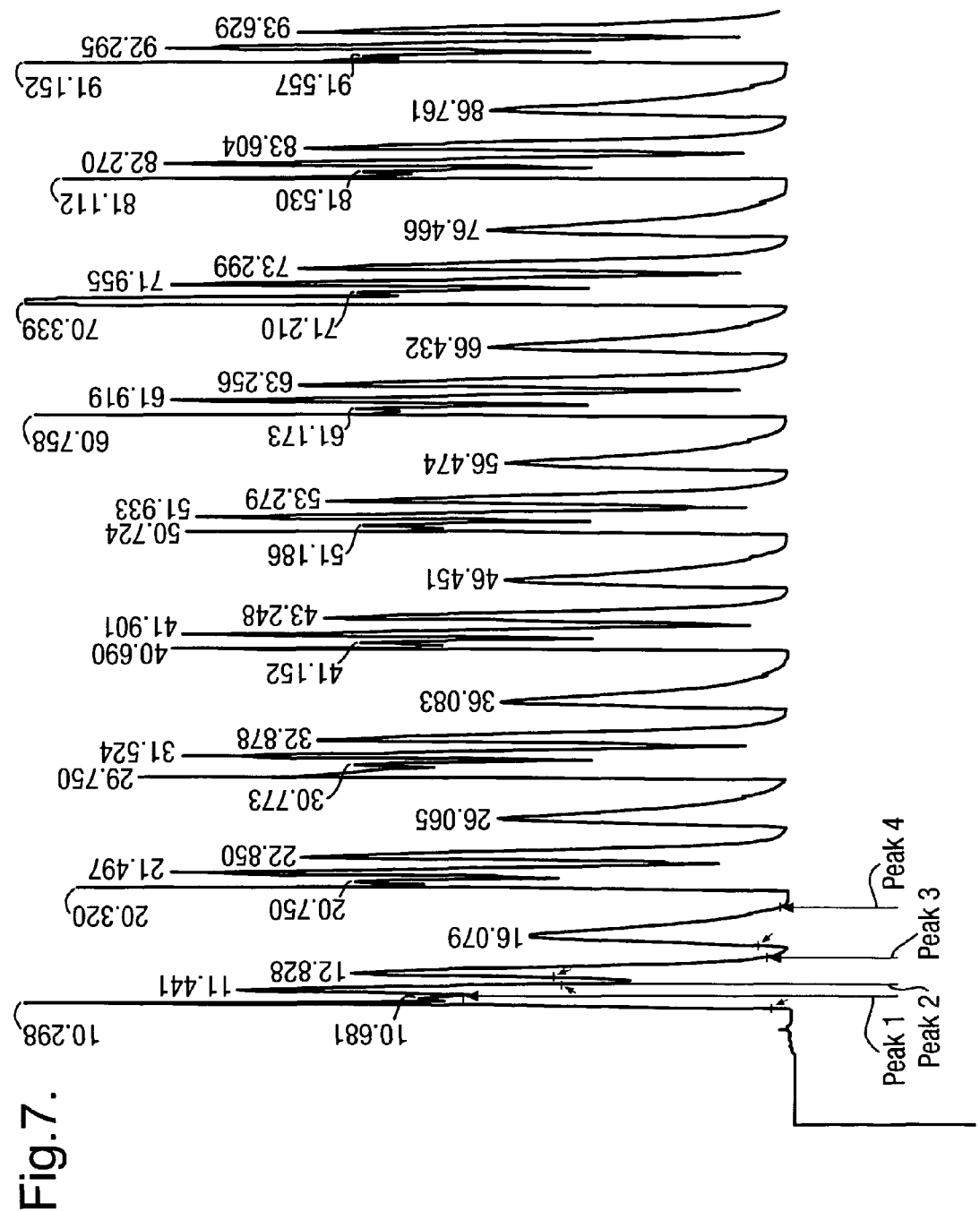

2. In order to purify 100 mg of each enantiomer it was necessary to dissolve 800 mg of the methoxamine racemate in 80 ml of mobile phase. A 22.1×250 mm column packed with 5 micron Cyclobond 1 2000 RSP (Astec catalog #20344) was conditioned at 20 ml/minute with the mobile phase used above on the analytical column. The column was monitored at 254 nm UV and 2.5 mg injections were made every 20 minutes for a total of 320 injections. Cuts to collect the separated peaks were made according to the arrows in FIG. 7. Peaks 1 and 2 each were shaved and pooled while Peaks 3 and 4 were individually collected and pooled.

Recovery of Separated Peaks on a C18 Column.

1. A 22.1×250 mm C 18 column packed with 5 micron stationary phase was washed with water. The pH of the pooled solutions was adjusted to 7.0 with triethylamine and the volume doubled with HPLC grade water.

2. The pH adjusted sample was then pumped onto the C18 column at 10 ml/min.

3. The flask was rinsed with water and the rinse was also passed through the column. Additional water was passed through the column until all the triethylamine acetate was washed from the column, as measured by a return to a stable baseline under 254 nm UV detection. The sample was eluted by pumping methanol through the column. Completion of the elution was observed from the UV monitoring at 254 nm.

4. After elution the column was again washed with water in preparation for processing of the next sample. Peaks 1, 2, 3 and peak 4 were all individually treated in this manner.

5. The recovered sample in methanol was concentrated to dryness under water bath conditions at 40° C.

Treatment of Peaks 3 and 4.

Figure 8:
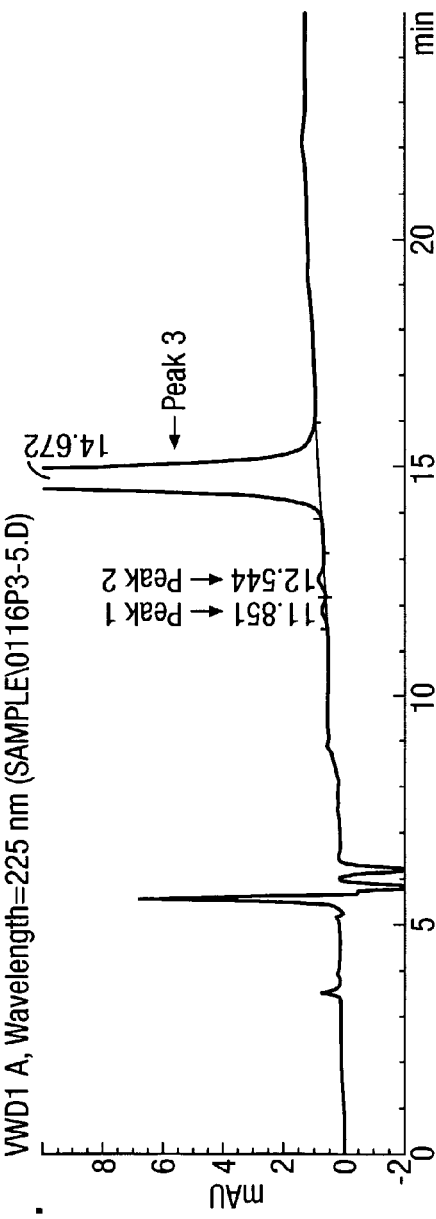
Figure 9:
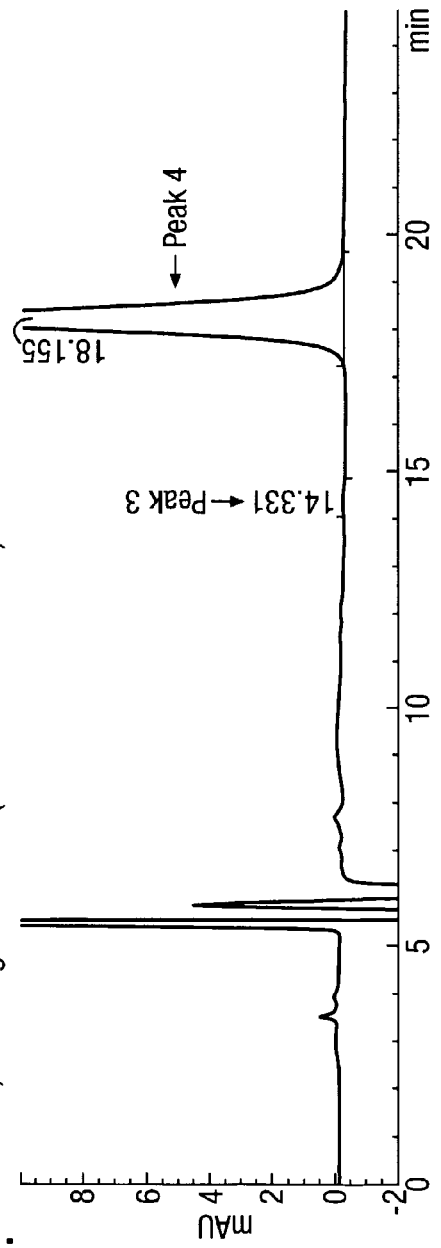
Figure 12:
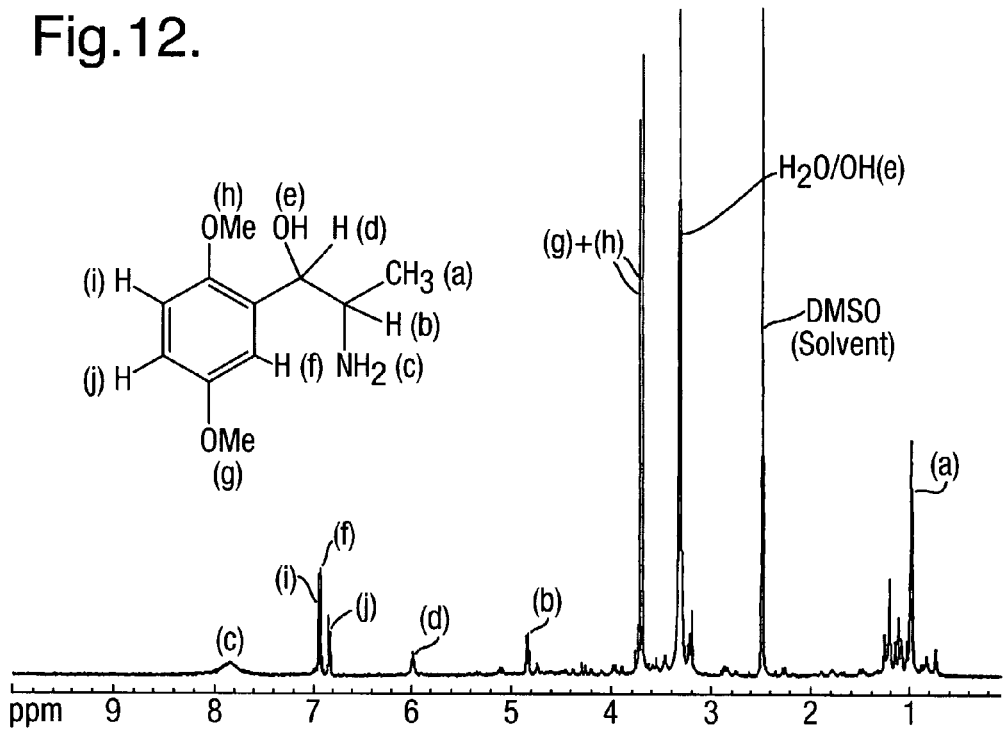
FIG. 12 shows the nmr spectrum of peak 1, FIG. 13 the nmr spectrum of peak 3, FIG. 14 the nmr spectrum of peak 2 and FIG. 15 the nmr spectrum of peak 4.
Figure 13:
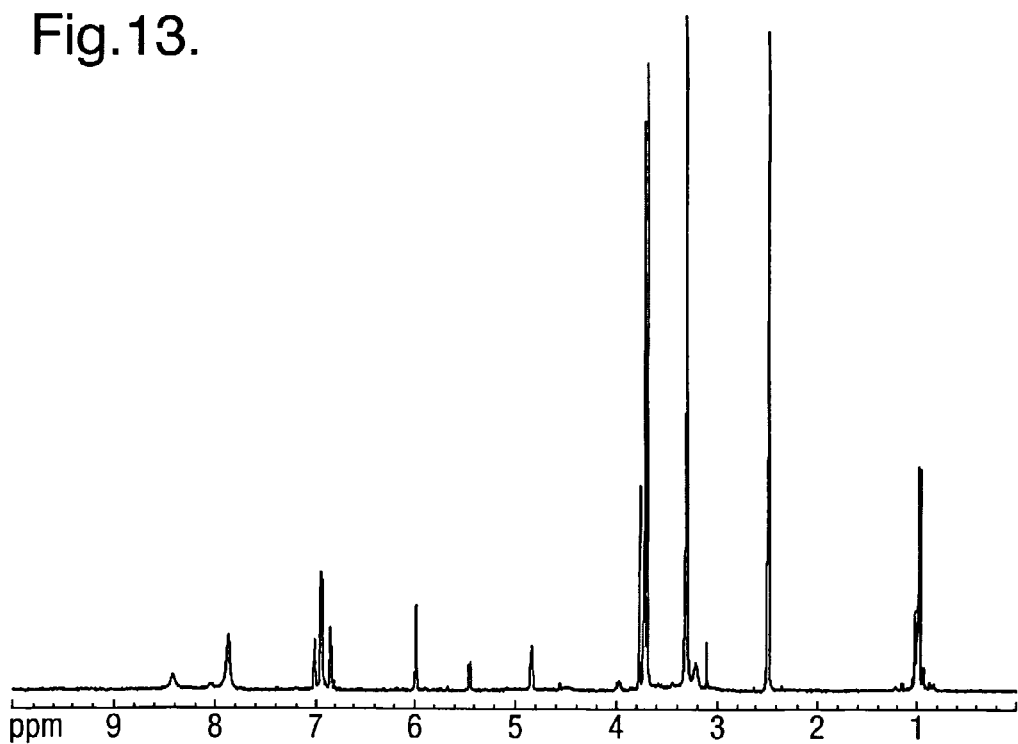
Figure 14:
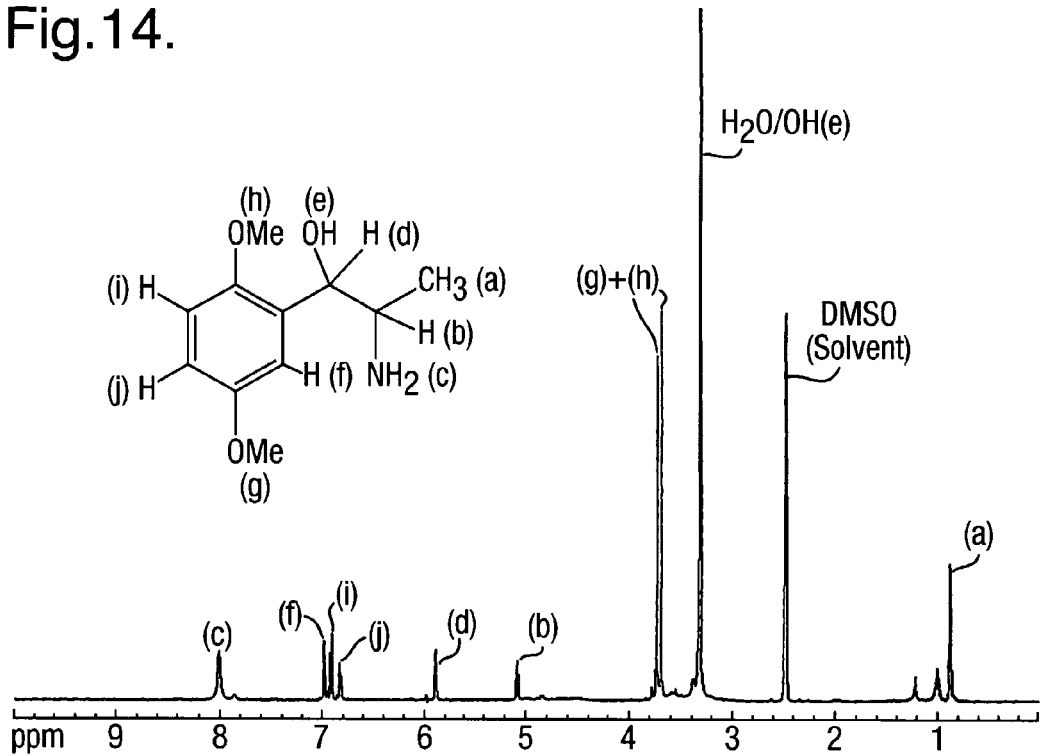
Figure 15:
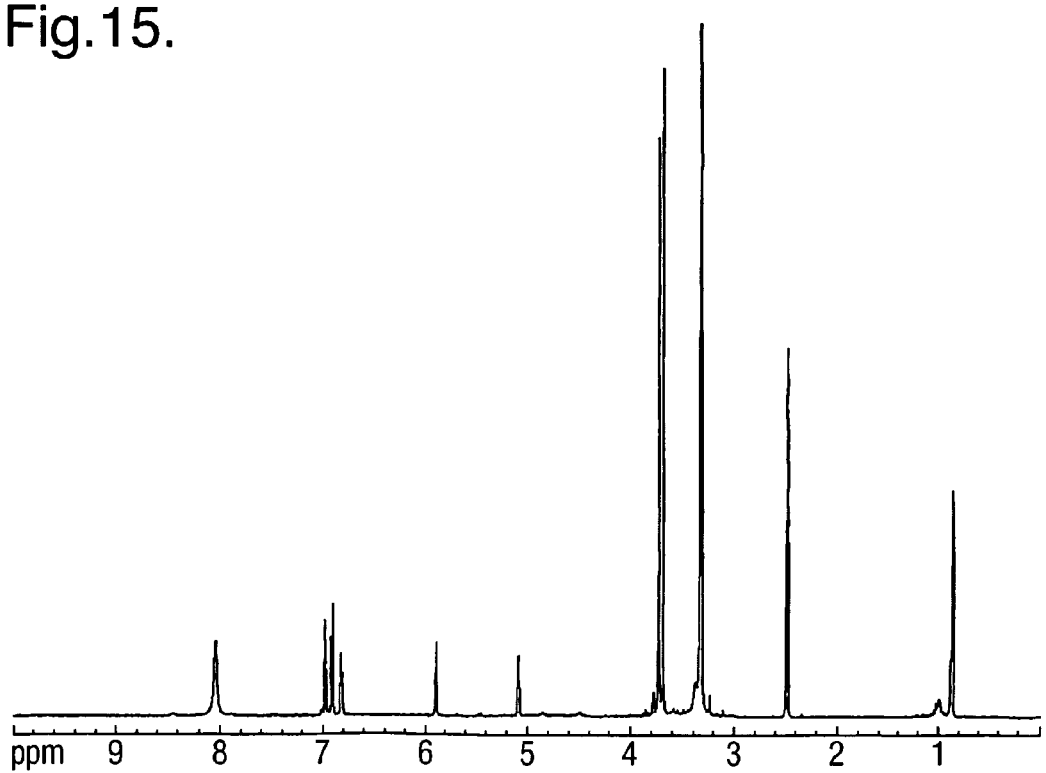
Figure 16:
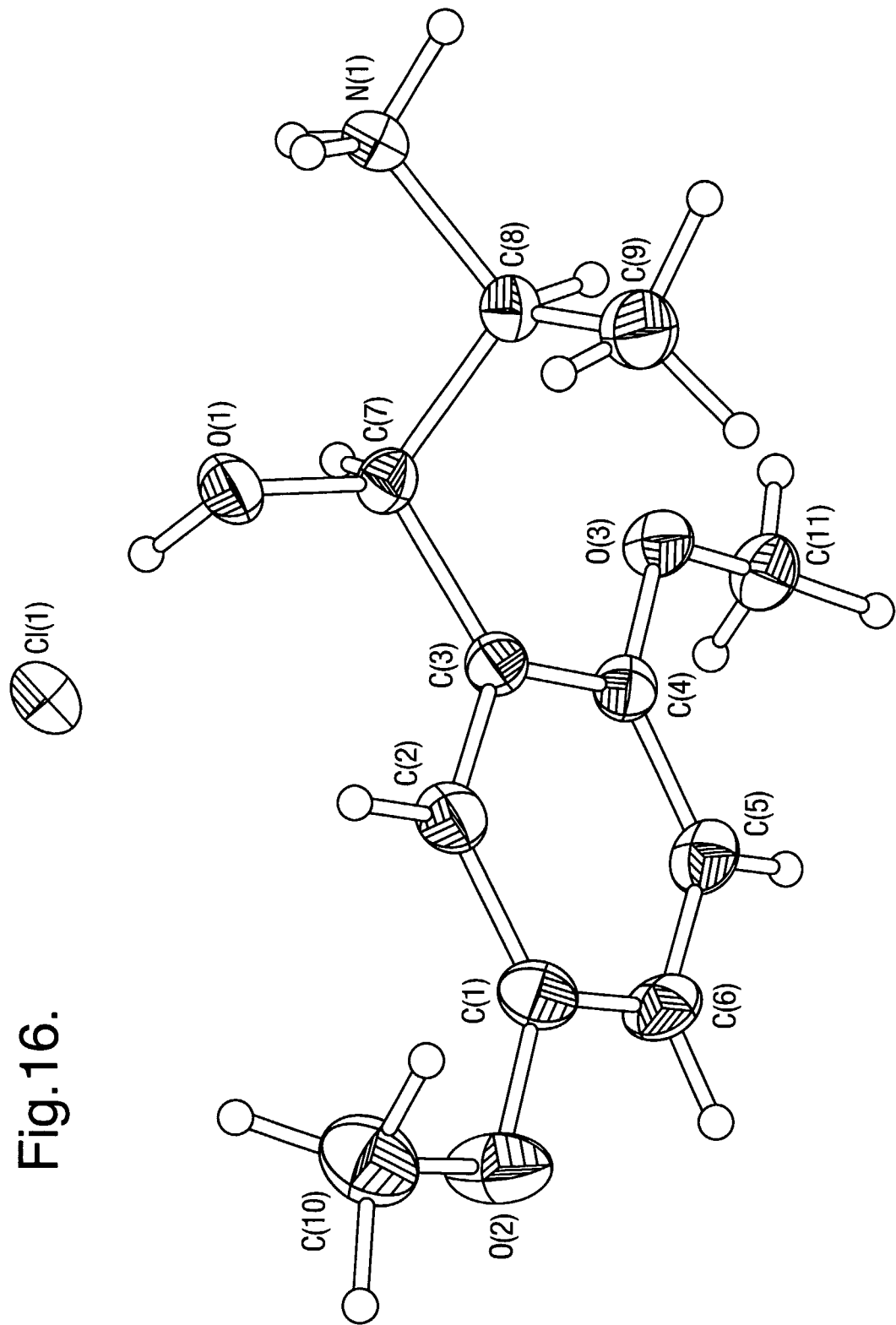
FIG. 16 shows the stereochemical structure of 1R,2S-methoxamine (peak 2).

The residue from the methanol/C18 treatment was redissolved in 20 ml methanolic JCL (0.1%) and re-evaporated. The residue was triturated with ether (~15 ml) to obtain a powder. FIG. 8 is the assay for the purity of peak 3 (140 mg) and FIG. 9 is the assay for the purity of peak 4 (105 mg).

Further Purification of Peaks 1 and 2.

1. A 250×30 mm, 5 micron C18 column was equilibrated with a mobile phase: 20/80; 0.1% TEAA, pH 4.1 at a flow rate of 35 ml/min.

2. The residue from the recovered C18 column of pooled peaks 1 and 2 was dissolved in mobile phase and 1 mg stacked injections were made.

Recovery of Peak 1 and Peak 2.

1. The 22.1×250 mm column was conditioned with HPLC grade water.

2. The collected and pooled fractions of peak 1 and peak 2 were pH adjusted to 7.0 with triethylamine and the volume doubled with HPLC grade water.

3. The individual pooled fractions were pumped onto the C18 column, the column was then washed with water to remove the buffer and finally eluted with methanol.

4. The methanol was concentrated to dryness under water bath conditions at 40° C.

5. The methanol residue was redissolved in methanolic HCL and reconcentrated.

6. The residue from this treatment was triturated with ether to obtain a powder, peak 1 (44 mg) and the yield of peak 1 was 44 mg and of peak 2 was 29 mg.

Second Run of Peaks 1 and 2

The first samples of peak 1 and peak 2 that were submitted had low yield and lower purity than targeted and the powder was highly colored (pale green). It was believed that the repeated treatment from the first run may have led to some auto-oxidation. It was therefore decided to rerun the RSP column on the total racemate first. In this case peaks 1 and 2 were closely shaved so that they did not have to be rechromatographed.

The resulting recovery of peaks 1 and peak 2 as processed above was substantially higher and the colour substantially lighter. FIG. 10 shows the purity of peak 1 (45 mg) and FIG. 11 the purity of peak 2 (34 mg).

Characterisation of the Isomers by NMR Spectroscopy

Proton mnr spectra of the four fractions (peaks 1 to 4) in dimethylsulphoxide ($d_6$-DMSO) were obtained at room temperature using a Briker DRX 500 MHz nmr spectrometer), see FIGS. 12 to 15. Although the resonances could be assigned to particular proton environments in the structures, there was no way of assigning the relative stereochemistry.

The spectra for peak 1 (FIG. 12) and peak 3 (FIG. 13) are almost identical, in particular the diagnostic peaks at 4.8 ppm (identified as b) in both the structure and the nmr spectrum and 6.0 ppm (d), making these enantiomeric pairs. Likewise, peak 2 (FIG. 14) and peak 4 (FIG. 15) are also quite similar to each other in the position of b and d, again making them enantiomeric pairs, but different from peaks 1 and 3. Even the amine proteins above 7.5 ppm (c) can be similarly matched. Exchangeable environments such as those due to amine or alcohol resonances are often not reliable as their chemical shift position is dependent on concentration and temperature. The alcohol OH resonance is indistinguishable from the residual water resonance at 3.3 ppm by virtue of chemical exchange. Accordingly, peaks 1 and 3 are diastereomers of peaks 2 and 4.

Example 3

Synthesis of 1R,2S-Methoxamine (S)—N-Methoxycarbonyl Alanine

To a stirred solution of L-alanine (300 g, 3.37 mol sodium hydroxide (1N, 1800 cm$^3$) at 0° C. in an ice bath was added dropwise, over 2 hours, methyl chloroformate (274 cm$^3$, 3.54 mol). The pH of the solution was maintained at 9 by the addition of sodium hydroxide (5N). The reaction mixture was stirred at 0° C. for 3 hours whereupon it was acidified to pH 1 by the addition of phosphoric acid solution (15%) and extracted with diethyl ether (5×1000 cm$^3$). The combined organic extracts were dried (MgSO$_4$) and concentrated under reduced pressure to yield the product as a viscous green oil (386 g, 78%). $^1$H NMR (250 MHz; C$^2$HCl$_3$) 1.48 (3H, d, J7.25, CH$_3$), 3.72 (3H, s, COCH$_3$), 4.40 (1H, quintet, J7.25, CH), 5.31 (1H, bs, NH).

(S)—N-Methoxycarbonyl alaninedimethylamide

To a stirred solution of MeOC-alanine (227 g, 1.54 mol) and dimethylformamide (DMF) (25 cm$^3$) in dry dichlorouerthane (DCM) (2000 cm$^3$) at 0° C. was added dropwise oxalyl chloride (146 cm$^3$, 1.62 mol) over a period of 2 hours. The solution was stirred at 0° C. until the evolution of gasses ceased whereupon a basic solution of dimethylamine (676 g, 7.70 mol) in NaOH (3 N, 2000 cm$^3$) was added. The aqueous layer was extracted with diethyl ether (2×500 cm$^3$) and the combined organic layers dried (MgSO$_4$) and concentrated under reduced pressure to give the product as a white crystalline solid which required no further purification (230 g, 86%). $^1$H NMR (250 MH$_z$; C$^2$HCl$_3$) 1.33 (3H, d, J6.75, CH$_3$), 2.99 3 H, s, OCH$_3$) 3.08, (3H, s, OCH$_3$), 3.66 (3H, s, COCH$_3$), 4.66 (H, quintet, J7.00, CH), 5.75 (1H, d, J5.75, NH).

(S)-2-[(Methoxycarbonyl)amino]-1-(2,5-dimethoxyphenyl)-1-propanone

To a THF (1000 cm$^3$) solution of bromo-2,5-dimethoxybenzene (55 g, 0.25 mol) at −20° C. under nitrogen was added n-butyl lithium (100 cm$^3$, 2.5 M in hexanes, 0.25 mol). The mixture was stirred at −20° C. for 0.75 hours, whereupon a THF (100 cm$^3$) solution of amide (30 g, 0.17 mol) was added via cannula. The solution was stirred at −20° C. for 2 hours and was then allowed to warm to room temperature over 1 hour and quenched by the addition of ammonium chloride solution (700 cm$^3$). The solution was diluted with diethyl ether (1000 cm$^3$) and the organic layer was dried (MgSO$_4$) and concentrated under reduced pressure to give a yellow oil. The product was purified by dry flash chromatography on silica (eluant 4:1 hexane/ethyl acetate then 3:2 hexane/ethyl acetate) to give the product as a white crystalline solid (45 g, 98%). $^1$H NMR (250 MHz; C$^2$HCl$_3$) 1.36 (3H, d, J7.0, CH$_3$), 3.70 (3H, s, COCH$_3$), 3.82 (3H, s, OCH$_3$), 3.92 (3H, s, OCH$_3$), 5.43 (1H, quintet, J7.3, H-2), 5.80 (1H, bs, NH), 6.94 (1H, d, J 9.0, ArH), 7.10 (1H, dd, J 9.0, 3.3, ArH), 7.32 (1H, d, J 3.3, ArH).

(1R,2S)-2-[(Methoxycarbonyl)amino]-1-(2,5-dimethoxyphenyl)-1-propanol

To a stirred solution of ketone i.e. (S)-2-[(methoxycarbonyl)amino]-1-(2,5-dimethoxyphenyl)-1-propanone (20 g, 74.9 mmol) and dimethylphenyl silane (10.7 g, 78.6 mmol) in dry DCM (500 cm$^3$) at 0° C. in an ice bath was added dropwise trithioroacetic acid (TFA) (50 cm$^3$). The solution was stirred at 0° C. for 1 h and then quenched by the addition of sodium hydroxide (500 cm$^3$, 1N). The organic layer was dried and concentrated under reduced pressure to give a yellow oil which solidified on standing. This solid was crystallized from ether/hexane to give the product as a white crystalline solid (15.6 g, 75%). $^1$H NMR (250 MHz; C$^2$HCl$_3$) 1.03 (3H, d, J7.0, CH$_3$), 3.04 (1H, d, J4.3, OH), 3.68 (3H, s, COCH$_3$), 3.78 (3H, s, OCH$_3$), 3.80 (3H, s, OCH$_3$), 3.94-3.99 (1H, m, H-2), 5.05-5.15 (2H, m, H-1 and NH), 6.72-6.85 (2H, m, ArH) 6.97 (1H, d, J 2.0, ArH).

(1,R,2S)-Methoxamine

To a stirred solution of methoxycarbonyl (MeOC) protected alcohol i.e. (1R,2S)-2-[(methoxycarbonyl)amino]-1-(2,5-dimethoxyphenyl)-1-propanol (4.0 g, 14.9 mmol) in methanol (175 cm$^3$) was added a solution of KOH (4.06 g, 72.8 mmol in water (60 cm$^3$). The solution was cooled and acidified with phosphoric acid (15% v/v). The solution was extracted with DCM (2×50 cm$^3$) and the aqueous layer basified by the addition of K$_2$CO$_3$. The aqueous layer was extracted with diethyl ether (5×50 cm$^3$) and the combined ethereal extracts dried (MgSO$_4$) and concentrated under reduced pressure to give the product as a clear yellow oil (1.9 g, 61%), $^1$H NMR (250 MHz; C$^2$HCl$_3$) 0.84 (3H, d, J 7.0, CH$_3$), 3.19-3.22 (1H, m, H-2), 3.71 (6H, s, 2×OCH$_3$), 4.67 (1H, d, J 5.0, H-1), 6.66-6.72 (2H, m, ArH), 6.92 (1H, d, J 2.5, ArH).

(1R,2S)-Methoxamine hydrochloride

To an ice cooled solution of (1R,2S)-methoxamine (1.9 g, 9.00 mmol) in anhydrous diethyl ether (30 cm$^3$) was passed a stream of dry HCl gas for 45 mins. The resultant precipitate was filtered by suction, washed with cold diethyl ether and dried under nitrogen to yield the title compound as a white solid. (1.5 g, 68%). $^1$H NMR (250 MHz; [C$^2$H$_3$]$_2$50) 0.89 (3H, d, J 6.8, CH$_3$), 3.37-3.42 (1H, m, H-2), 3.71 (3H, s, OCH$_3$), 3.75 (3H, s, OCH$_3$), 5.12 (1H, s, H-1), 5.92 (1H, d, J 4.3, OH), 6.84 (1H, dd, J 8.8, 3.0, ArH), 6.92-7.00 (2H, m, ArH); HPLC.

Analytical Method for the Analysis of Methoxamine

The following method was used to analyse methoxamine samples.
Method
Column: Cyclobond I RSP 250×4.6 mm
Column temperature: 23° C.
Mobile phase: 0.1% Tetraethylammonium pH 4.1*95% v/v : Acetonitrile 5% v/v
Flow rate: 0.6 ml/min
Solution
Concentration: 5 mg/l
Injection volume: 2.5 μl to 20 μl
Detection: UV 230 nm
*Tetraethylammonium acetate pH 4.1 was prepared fresh daily.

Example 4

Stereochemical Characterisation of 1R,2S-Methoxamine by Single Crystal X-Ray Analysis Single crystal X-ray analysis is the definitive tool for structural assignment. The hydrochloride salt of the putative 1R,2S isomer of methoxamine (also called the L-erythro isomer) was synthesised as described in Example 3. The hydrochloride salt of the putative 1R,2R (D-threo isomer was synthesised according to a modification of the Fujita and Hyama method, in which sodium borohydride was used as reducing agent to produce a mixture of 1R,2R-(D-threo) and 1R,2S-(D-erythro) isomers. The 1R,2R-isomer was purified using flash chromatography on a silica column.

The two compounds were crystallised from a methanol/ethyl-acetate solution in an atmosphere of hexane. The resulting crystals were very fine plates that gave excellent data from which the structures were solved with a reliable refinement factor. The X-ray crystallography was carried out using a Nonius KappaCCD. The atomic coordinates and equivalent isotropic displacement parameters are given in Table 2. The crystal data and structure refinement are given in Table 3. Bond lengths and angles are given in Table 4. Anisotropic displacement parameters and given in Table 5 and hydrogen coordinates and isotropic displacement parameters in Table 6.

TABLE 2

Atomic coordinates [×10$^4$] and equivalent isotropic displacement parameters [Å$^2$ × 10$^3$] for nb0103. U(eq) is defined as one third of the trace of the orthogonalized U$_{ij}$ tensor.

|       | x       | y       | z       | U(eq)  |
|-------|---------|---------|---------|--------|
| Cl(1) | −3293(1)| 5351(1) | 670(1)  | 29(1)  |
| O(1)  | −889(3) | 2022(2) | 957(1)  | 28(1)  |
| O(2)  | 2949(3) | 4524(2) | 3752(1) | 38(1)  |
| O(3)  | −4256(3)| −221(2) | 3208(1) | 30(1)  |
| N(1)  | −1904(3)| −935(2) | 408(1)  | 24(1)  |
| C(1)  | 1183(4) | 3350(3) | 3583(2) | 28(1)  |
| C(2)  | 583(4)  | 2757(3) | 2715(1) | 25(1)  |
| C(3)  | −1260(4)| 1583(3) | 2599(1) | 23(1)  |
| C(4)  | −2503(4)| 969(3)  | 3369(1) | 24(1)  |
| C(5)  | −1909(4)| 1570(3) | 4237(1) | 27(1)  |
| C(6)  | −105(4) | 2762(3) | 4335(1) | 29(1)  |
| C(7)  | −2078(4)| 1072(3) | 1638(1) | 23(1)  |
| C(8)  | −1501(4)| −703(3) | 1421(1) | 24(1)  |
| C(9)  | 1147(4) | −1230(3)| 1640(2) | 38(1)  |
| C(10) | 4470(4) | 5030(3) | 3006(2) | 37(1)  |
| C(11) | −5712(4)| −746(3) | 3969(2) | 33(1)  |

TABLE 3

Crystal data and structure refinement for nb0103.

| Identification code | nb0103 |
|---|---|
| Empirical formula | C$_{11}$H$_{18}$ClNO$_3$ |
| Formula weight | 247.71 |
| Temperature | 180(2) K |
| Wavelength | 0.7107 Å |
| Crystal system | Monoclinic |
| Space group | P2$_1$ |
| Unit cell dimensions | a = 5.3331(3) Å α = 90° |
|  | b = 8.2342(6) Å β = 90.195(4)° |
|  | c = 14.6198(7) Å γ = 90° |
| Volume | 642.01(7) Å$^3$ |
| Z | 2 |
| Density (calculated) | 1.281 Mg/m$^3$ |
| Absorption coefficient | 0.291 mm$^{-1}$ |
| F(000) | 264 |
| Crystal size | 0.23 × 0.18 × 0.01 mm |
| θ range for data collection | 3.73 to 27.44° |
| Index ranges | −6 ≤ h ≤ 6, −10 ≤ k ≤ 9, −17 ≤ l ≤ 18 |
| Reflections collected | 4436 |
| Independent reflections | 2536 (R$_{int}$ = 0.0288) |
| Absorption correction | Semi-empirical from equivalents |
| Max. and min. transmission | 0.997 and 0.957 |
| Refinement method | Full-matrix least-squares on F$^2$ |
| Data/restraints/parameters | 2536/1/153 |
| Goodness-of-fit on F$^2$ | 1.099 |
| Final R indices [I > 2σ(I)] | R1 = 0.0331, wR2 = 0.0832 |
| R indices (all data) | R1 = 0.0379, wR2 = 0.0861 |
| Absolute structure parameter | 0.00(6) |
| Largest diff. peak and hole | 0.188 and −0.212 eÅ$^{-3}$ |

TABLE 6

Bond lengths [Å] and angles [°] for nb0103.

| O(1)—C(7) | 1.417(2) | O(1)—H(1)  | 0.86(3)  |
|-----------|----------|------------|----------|
| O(2)—C(1) | 1.372(3) | O(2)—C(10) | 1.423(3) |
| O(3)—C(4) | 1.375(3) | O(3)—C(11) | 1.426(3) |

TABLE 6-continued

Bond lengths [Å] and angles [°] for nb0103.

| | | | |
|---|---|---|---|
| N(1)—C(8) | 1.509(2) | N(1)—H(1A) | 0.9100 |
| N(1)—H(1B) | 0.9100 | N(1)—H(1C) | 0.9100 |
| C(1)—C(6) | 1.386(3) | C(1)—C(2) | 1.396(3) |
| C(2)—C(3) | 1.388(3) | C(2)—H(2A) | 0.9500 |
| C(3)—C(4) | 1.401(3) | C(3)—C(7) | 1.529(3) |
| C(4)—C(5) | 1.398(3) | C(5)—C(6) | 1.381(3) |
| C(5)—H(5A) | 0.9500 | C(6)—H(6A) | 0.9500 |
| C(7)—C(8) | 1.527(3) | C(7)—H(7A) | 1.0000 |
| C(8)—C(9) | 1.511(3) | C(8)—H(8A) | 1.0000 |
| C(9)—H(9A) | 0.9800 | C(9)—H(9B) | 0.9800 |
| C(9)—H(9C) | 0.9800 | C(10)—H(10A) | 0.9800 |
| C(10)—H(10B) | 0.9800 | C(10)—H(10C) | 0.9800 |
| C(11)—H(11A) | 0.9800 | C(11)—H(11B) | 0.9800 |
| C(11)—H(11C) | 0.9800 | | |
| C(7)—O(1)—H(1) | 104.6(18) | C(1)—O(2)—C(10) | 117.49(17) |
| C(4)—O(3)—C(11) | 117.06(17) | C(8)—N(1)—H(1A) | 109.5 |
| C(8)—N(1)—H(1B) | 109.5 | H(1A)—N(1)—H(1B) | 109.5 |
| C(8)—N(1)—H(1C) | 109.5 | H(1A)—N(1)—H(1C) | 109.5 |
| H(1B)—N(1)—H(1C) | 109.5 | O(2)—C(1)—C(6) | 116.45(19) |
| O(2)—C(1)—C(2) | 124.41(19) | C(6)—C(1)—C(2) | 119.1(2) |
| C(3)—C(2)—C(1) | 120.92(18) | C(3)—C(2)—H(2A) | 119.5 |
| C(1)—C(2)—H(2A) | 119.5 | C(2)—C(3)—C(4) | 119.34(18) |
| C(2)—C(3)—C(7) | 120.18(17) | C(4)—C(3)—C(7) | 120.27(19) |
| O(3)—C(4)—C(5) | 124.01(18) | O(3)—C(4)—C(3) | 116.32(18) |
| C(5)—C(4)—C(3) | 119.7(2) | C(6)—C(5)—C(4) | 120.07(18) |
| C(6)—C(5)—H(5A) | 120.0 | C(4)—C(5)—H(5A) | 120.0 |
| C(5)—C(6)—C(1) | 120.84(19) | C(5)—C(6)—H(6A) | 119.6 |
| C(1)—C(6)—H(6A) | 119.6 | O(1)—C(7)—C(8) | 106.94(16) |
| O(1)—C(7)—C(3) | 111.52(18) | C(8)—C(7)—C(3) | 113.41(18) |
| O(1)—C(7)—H(7A) | 108.3 | C(8)—C(7)—H(7A) | 108.3 |
| C(3)—C(7)—H(7A) | 108.3 | N(1)—C(8)—C(9) | 107.55(17) |
| N(1)—C(8)—C(7) | 107.30(17) | C(9)—C(8)—C(7) | 114.8(2) |
| N(1)—C(8)—H(8A) | 109.0 | C(9)—C(8)—H(8A) | 109.0 |
| C(7)—C(8)—H(8A) | 109.0 | C(8)—C(9)—H(9A) | 109.5 |
| C(8)—C(9)—H(9B) | 109.5 | H(9A)—C(9)—H(9B) | 109.5 |
| C(8)—C(9)—H(9C) | 109.5 | H(9A)—C(9)—H(9C) | 109.5 |
| H(9B)—C(9)—H(9C) | 109.5 | O(2)—C(10)—H(10A) | 109.5 |
| O(2)—C(10)—H(10B) | 109.5 | H(10A)—C(10)—H(10B) | 109.5 |
| O(2)—C(10)—H(10C) | 109.5 | H(10A)—C(10)—H(10C) | 109.5 |
| H(10B)—C(10)—H(10C) | 109.5 | O(3)—C(11)—H(11A) | 109.5 |
| O(3)—C(11)—H(11B) | 109.5 | H(11A)—C(11)—H(11B) | 109.5 |
| O(3)—C(11)—H(11C) | 109.5 | H(11A)—C(11)—H(11C) | 109.5 |
| H(11B)—C(11)—H(11C) | 109.5 | | |

Symmetry Transformations Used to Generate Equivalent Atoms:

TABLE 4

Anisotropic displacement parameters [Å² × 10³] for nb0103.
The anisotropic displacement factor exponent takes the form:
$-2\pi^2 [(ha^*)^2 U_{11} + \ldots + 2hka^*b^*U_{12}]$

| | U11 | U22 | U33 | U23 | U13 | U12 |
|---|---|---|---|---|---|---|
| Cl(1) | 32(1) | 21(1) | 33(1) | 1(1) | 0(1) | −2(1) |
| O(1) | 43(1) | 19(1) | 21(1) | 1(1) | 8(1) | 2(1) |
| O(2) | 41(1) | 43(1) | 30(1) | −13(1) | 7(1) | −15(1) |
| O(3) | 36(1) | 34(1) | 21(1) | 1(1) | 6(1) | −10(1) |
| N(1) | 28(1) | 19(1) | 24(1) | −2(1) | −1(1) | 0(1) |
| C(1) | 29(1) | 26(1) | 30(1) | −5(1) | 3(1) | 1(1) |
| C(2) | 29(1) | 24(1) | 23(1) | −2(1) | 5(1) | 2(1) |
| C(3) | 28(1) | 20(1) | 20(1) | 0(1) | 2(1) | 2(1) |
| C(4) | 24(1) | 24(1) | 23(1) | 0(1) | 1(1) | 2(1) |
| C(5) | 30(1) | 33(1) | 19(1) | 1(1) | 6(1) | 2(1) |
| C(6) | 34(1) | 34(1) | 20(1) | −5(1) | 2(1) | 2(1) |
| C(7) | 29(1) | 22(1) | 18(1) | 2(1) | 2(1) | 0(1) |
| C(8) | 33(1) | 20(1) | 20(1) | 3(1) | 0(1) | −1(1) |
| C(9) | 44(1) | 34(1) | 35(1) | −6(1) | −13(1) | 14(1) |
| C(10) | 36(1) | 33(2) | 41(1) | −3(1) | 7(1) | −4(1) |
| C(11) | 32(1) | 39(1) | 28(1) | 7(1) | 5(1) | −3(1) |

TABLE 5

Hydrogen coordinates (×10⁴) and isotropic displacement parameters (Å² × 10³) for nb0103.

| | x | y | z | U(eq) |
|---|---|---|---|---|
| H(1) | −1670(50) | 2940(40) | 968(18) | 40(8) |
| H(1A) | −3403 | −494 | 242 | 36 |
| H(1B) | −1905 | −2015 | 275 | 36 |
| H(1C) | −648 | −437 | 95 | 36 |
| H(2A) | 1447 | 3162 | 2196 | 30 |
| H(5A) | −2747 | 1158 | 4760 | 33 |
| H(6A) | 257 | 3184 | 4926 | 35 |
| H(7A) | −3930 | 1238 | 1584 | 27 |
| H(8A) | −2700 | −1412 | 1762 | 29 |
| H(9A) | 1427 | −2328 | 1403 | 56 |
| H(9B) | 1398 | −1226 | 2304 | 56 |
| H(9C) | 2335 | −478 | 1355 | 56 |
| H(10A) | 5757 | 5785 | 3227 | 55 |
| H(10B) | 3423 | 5573 | 2547 | 55 |
| H(10C) | 5279 | 4080 | 2731 | 55 |
| H(11A) | −6911 | −1575 | 3768 | 49 |
| H(11B) | −6623 | 181 | 4225 | 49 |
| H(11C) | −4602 | −1206 | 4438 | 49 |

Figure 17:
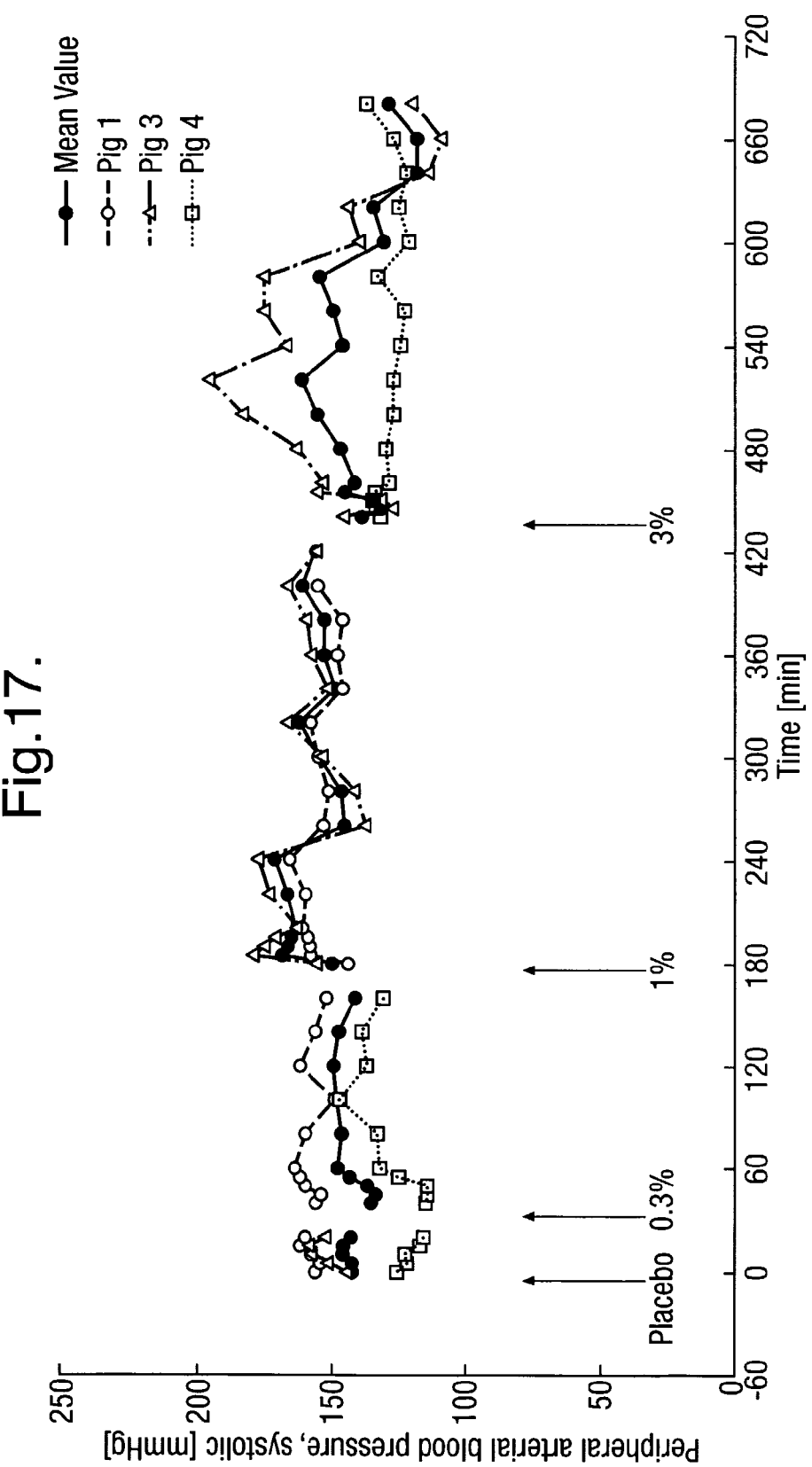
FIG. 17 shows the effect of 0.5 ml doses of placebo and of 0.3%, 1% 3% w/w 1R,2S-methoxamine gels on the peripheral systolic arterial blood pressure of pigs

These results enable the isomer synthesised in Example 3 and isolated by chromatography as peak 2 in Example 2 to be identified unequivocally as the 1R,2S-isomer of methoxamine. The structure of the isomer is shown in FIG. 17.

The crystallographic results and the deductions based on nmr spectroscopy described in Example 2 above allows the complete assignment of the methoxamine isomers as shown below:

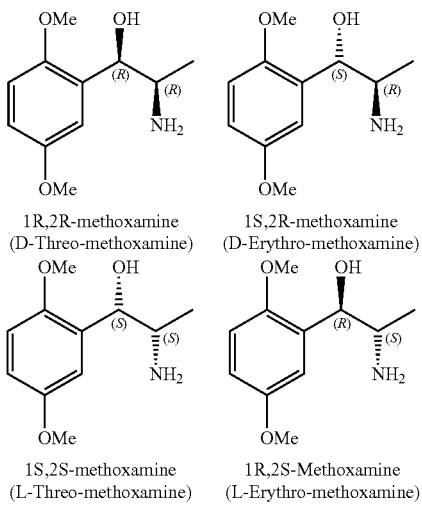

1R,2R-methoxamine (D-Threo-methoxamine)
1S,2R-methoxamine (D-Erythro-methoxamine)
1S,2S-methoxamine (L-Threo-methoxamine)
1R,2S-Methoxamine (L-Erythro-methoxamine)

Example 5

Examination of the Influence of 1R,2S-Methoxamine on Several Cardiovascular Parameters and the Mean Anal Resting Pressure (MARP) in Anaesthetised Pigs Following Topical Administration to the Anoderm Method The study was conducted according to the following protocol:

Test Substances:
a) Placebo in 4% w/w gel
b) 0.3% by weight 1R,2S-methoxamine in 4% w/w gel
c) 1% by weight 1R,2S-methoxamine in 4% w/w gel
d) 3% by weight 1R,2S-methoxamine in 4% w/w gel
The 4% w/w gel comprises 4 g of hydroxypropylmethyl cellulose in 96 ml of 0.5M acetate buffer. 1% by weight 1R,2S-methoxamine in 4% w/w gel comprises 1 g of 1R,2S-methoxamine in 99 g of the 4% gel.

Animals/Animal Maintenance

Göttingen-minipigs obtained from Ellegaard Göttingen Minipigs ApS, Soro Landevej 302, DK-4261 Dalmose, Denmark were used for the investigation. The animals, which were 4 to 5 months old, each had a body weight at the start of the investigation of 6.9 to 8.7 kg. Four male animals were used. Animal no. 2 was replaced by animal no. 4, see below.

Diet & Drinking Water

The diet for the minipigs was supplied by Ellegaard Göttingen Minipigs ApS. 200 g/kg b.w. of this food was offered to each pig twice daily during the adaptation period. In case of animals with poor appetite, the food was served for a longer period (up to 8 hours). On the day before dosing the minipigs did not receive any food. Tap water was offered ad libitum.

Housing

The pigs are kept singly in indoor pens with a floor space of approx. 3 m$^2$ on straw bedding maintained at a temperature of 22° C.±3° C. (maximum range) and a natural light cycle.

Anaesthesia

The minipigs were anaesthetised with a chloralose-urethane mixture (ratio 1+5). Additional anaesthesia was given when needed. To ensure a stable general condition of the minipig, blood gases and pH-value were measured in blood obtained from the right or left a. femoralis using a blood gas analyser ABL 70 (Radiometer, Copenhagen, Denmark) before start of experiment. Ringer solution (5 ml/kg b.w./h) was given continuously to compensate for fluid losses. The body temperature of the animals was maintained at 38° C. throughout the experiment of external heating.

Administration of Test Substances

The test substances were administered topically to the anoderm using a volume of 0.5 ml/animal. The interval between each observation period was 20 minutes. The administration was performed employing a 1 ml syringe inserted approximately 1 cm into the anal canal. The test substances were administered slowly while the syringe was rotated. After the preparation and a period of at least 15 minutes for stabilisation of the circulatory functions, the animals were treated with the placebo or the selected dose levels of the test substance by administration to the anoderm.

Before the first administration and at further suitable times after the administration, isoproterenol was administered intravenously for control purposes. Arterenol (norephinephrine hydrochloride, also known as L-noradrenaline) was administered for control purposes at the end of the study only after completing the collection of the blood samples for toxicokinetics.

Dose Levels

The study was carried out at the following dose levels:

| | Dose of test (content as w/w in substance 4% w/w gel) | | |
|---|---|---|---|
| | Pig No. 1 | Pig No. 3 | Pig No. 4 |
| Period I | 0.5 ml of placebo | 0.5 ml of placebo | 0.5 ml of placebo |
| Period II | 0.5 ml of 0.3% | 0.5 ml of 1% | 0.5 ml of 0.3% |
| Period III | 0.5 ml of 1% | 0.5 ml of 3% | 0.5 ml of 3% |

Pig No. 2 was replaced by pig no. 4 as the predose values for pig no. 2 were out of the normal range.

Parameters Measured

Preparations

Under anaesthesia, the minipigs were fixed in a dorsal position on the operating table.

Peripheral Arterial Blood Pressure

An intraarterial indwelling catheter (size 0.8×1.4 mm, B. Braun Melsungen AG, D-34212 Melsungen, Germany) was connected to a pressure transducer (DTX, Pfrimmer-Viggo, Erlangen, Germany) recording the systolic and diastolic arterial blood pressure in the right or left a. femoralis. The signal was boosed by a Hellige Servomed SMV 178 T amplifier (Hellige GmbH, D-79100 Freiburg, Germany). The blood pressure was recorded and monitored with a Hellige Cardiognost EK 512 P (paper speed: 2.5 mm/sec). Systolic and diastolic blood pressure [mmHg] were determined and the mean pressure was calculated according to the following formula:

Mean blood pressure [mmHg]=(systolic pressure+(2× diastolic pressure))/3

Heart Rate and Electrocardiography

ECG recordings were made using the standard limb leads I, II and III as well as augmented limb leads aVR, aVL and aVF. A standardisation of 10 mm/1 mV was used and a paper speed of 50 mm/sec. The recordings were carried out using a HEL-LIGE Marquette mac 5000 12SL. The recordings were examined visually for any arrhythmias and abnormalities of the electrical complexes. In addition, the following parameters were evaluated for limb lead II: Heart rate [beats/min]; P segment, [msec]; P-Q interval, [msec]; QRS complex [msec]; Q-T interval, [msec]. The QTc values [msec] were calculated according to the van de Water-formula: QTc=QT−0.087 (R-R distance−1000)

Mean and Resting Pressure

The anal resting pressure was measured by introduction of a manometric probe (Unisensor Microtipcatheter 8104-00-9409-D; Medical Measurement Systems b.v., Collosseum 25, NL-7521P.V. Enschede, The Netherlands) into the rectum three times. The anal resting pressure taken as a mean of these three measurements (MARP) was recorded with a Rikadenki Multipenrecorder.

Blood Sampling

Blood samples (5 ml/time-point) were taken immediately before and 10, 20, 40, 60, 90, and 120 minutes after start of administration, and were collected into lithium-heparin containers. The blood samples were immediately cooled at +2° C. to +8° C. by the use of an IsoTherm-Rack system (Eppendorf-Netheler-Hinz GmbH, D-22331 Hamburg, Germany) and the whole blood was processed for EDTA-plasma. Plasma was prepared by centrifugation (5 min, 4000 rpm, at +5° C.) and split into aliquots of approx. 1 ml each. Both plasma aliquots were immediately frozen at −80° C. at least and stored at this temperature until dispatch of one aliquot on dry ice for analysis.

The samples were labelled with the study number, species, animal number, sampling time, type of sample, date and dose level.

The samples were analysed for the methoxamine plasma levels. The results are presented in Appendix 3.

Macroscopical Inspection

A macroscopical inspection of the anoderm was carried out during the experiments. Any obvious irritation and/or erythema caused by the fairly low pH value of the test substance formulation was reported.

Evaluation and Time of Recording

For each measurement period the heart rate, ECG and the blood pressure in the a. femoralis were measured continuously and recorded immediately before and 5, 10, 15, 20, 40 and 60 minutes after start of administration for periods of approx. 30 sec, and then in intervals of 20 minutes until any effect had subsided.

Statistics

For each animal and dosage, the values obtained were compared to the start values. Mean values of the placebo control group were compared by means of the Student's paired t-test (Colquhoun, Lectures on Biostatistics, §10.6, 167-9 (1971), Clarendon Press, Oxford, England). The following limit was used: p=0.01 □t=4.604 (for 4 degrees of freedom). In the tables, significant differences (p≤0.01) from the start values are indicated. All calculations were performed to the highest possible degree of accuracy and then rounded to the reported number of decimal places. Hence, deviations of up to 1% may occur caused by rounding.

Study Termination

At the end of the study the animals were sacrificed.

Results

Peripheral Arterial Blood Pressure

The systolic, diastolic or mean blood pressure was not influenced by any of the tested dose levels of 1R,2S-methoxamine.

At all 1R,2S-methoxamine concentrations examined, changes in blood pressure were noted in individual animals. These changes are not considered to be substance-related but within the normal variability of long-term anaesthesia employing two animals per time-point.

Figure 18:
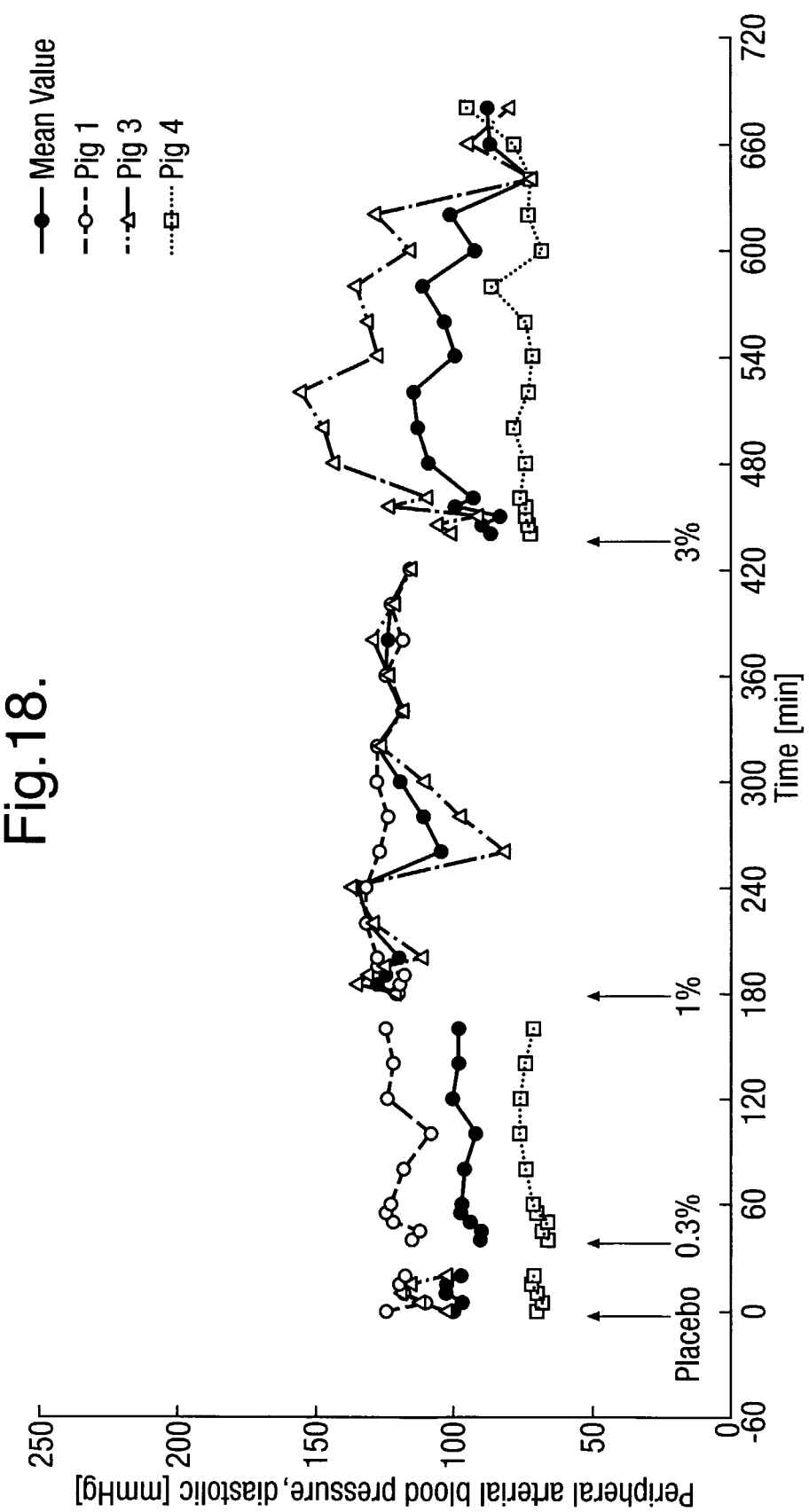
FIG. 18 shows the effect of 0.5 ml doses of placebo and of 0.3%, 1% and 3% w/w 1R,2S-methoxamine gels on the peripheral diastolic arterial blood pressure of pigs
Figure 19:
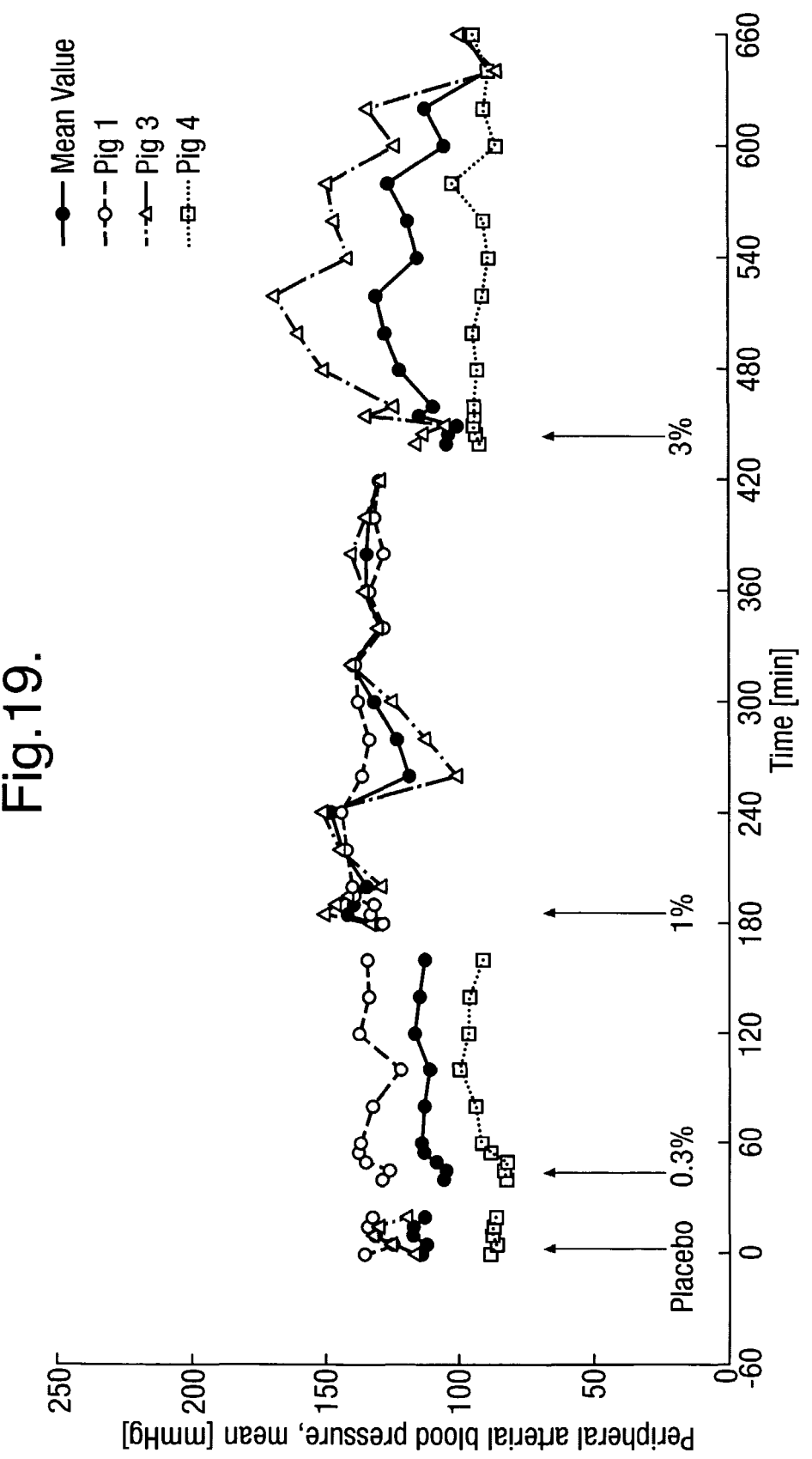
FIG. 19 shows the effect of 0.5 ml doses of placebo and of 0.3%, 1% and 3% w/w 1R,2S-methoxamine gels on the mean peripheral arterial blood pressure of pigs

Individual and mean values are presented. FIGS. 17 to 19. FIG. 17 shows the peripheral systolic arterial blood pressure, FIG. 18 shows the peripheral diastolic arterial blood pressure, and FIG. 19 shows the mean peripheral arterial blood pressure.

Mean Anal Resting Pressure (MARP)

Figure 20:
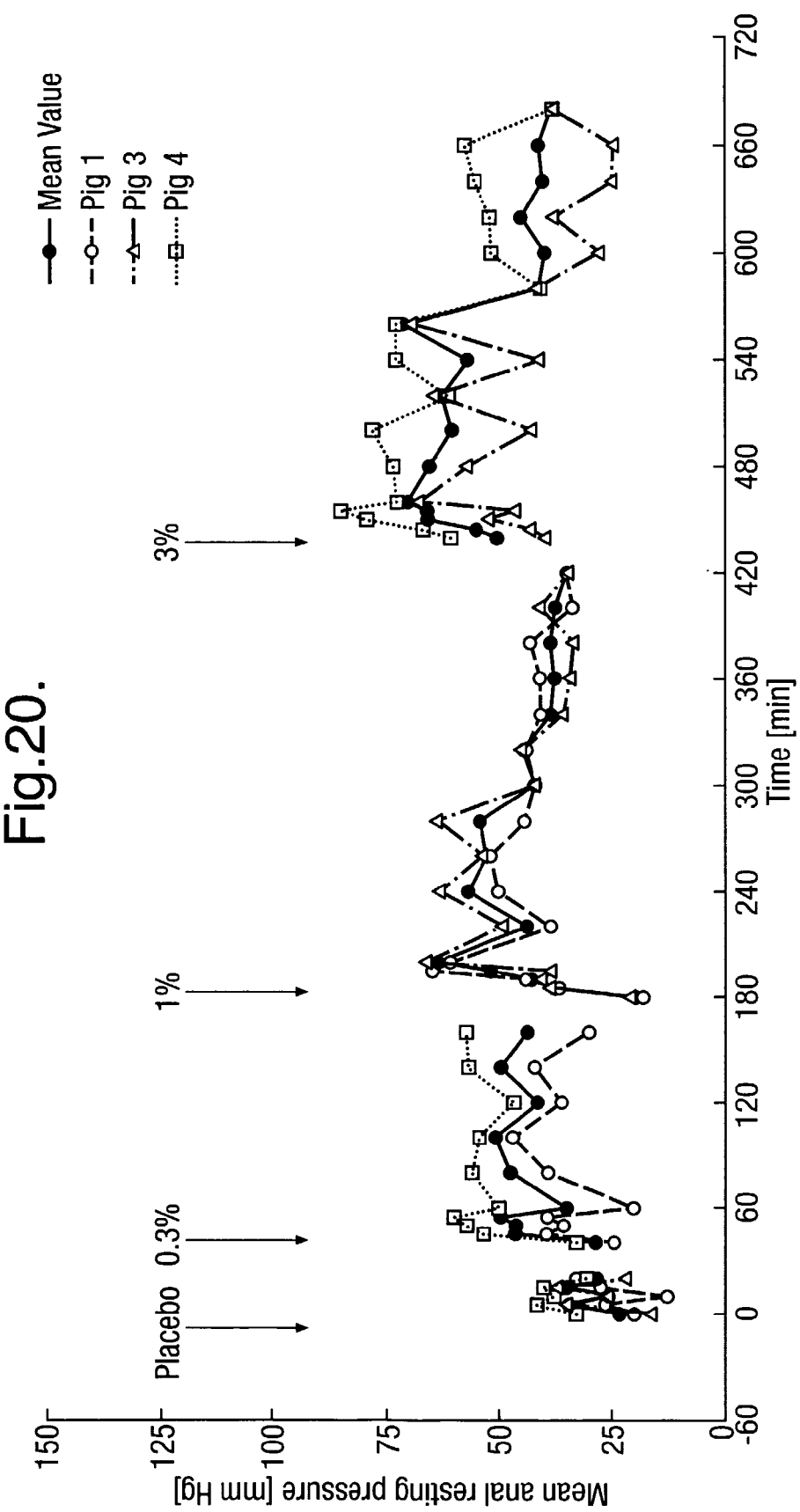
FIG. 20 shows the effect of 0.5 ml doses of placebo and of 0.3%, 1% and 3% w/w 1R,2S-methoxamine gels on the mean anal resting pressure of pigs

Treatment with 1R,2S-methoxamine at a concentration of 0.3% caused a dose-related increase in MARP to 50 mmHg (73% compared to the start value) on average for a period of 110 min starting 5 min after administration in both pigs. The 1% gel caused a further increase in MARP to 64 mmHg (a 227% increase) on average within 20 min after application. Administration of the 3% gel resulted in a dose-related increase in MARP to approx. 70 mmHg. Both animals were effected to a similar degree. Individual and mean values are presented in FIG. 20.

Heart Rate and ECG

The evaluation of the heat rate and the ECG parameters revealed no substance-related influence on P-segment, P-Q interval, Q-T interval QTc value, and QRS complex at any of the tested dose levels. In particular, no evidence was noted for a prolongation of the QT-interval.

Visual assessment of the ECG recordings did not reveal any ventricular premature complexes.

At 1R,2S-methoxamine concentrations of 1% and 3% an increase in the heart rate was observed to approx. 100 beats/min (a 29% increase) on average 2 hours after application in pigs 1 and 3. Afterwards a normalisation took place very gradually. These changes are not considered to be substance-related but within the normal variability of long-term anaesthesia employing two animals per time-point.

Similarly, all other changes noted in this study in individual animals are also not considered to be substance-related but within the normal variability of long-term anaesthesia employing two animals per time-point.

Figure 21:
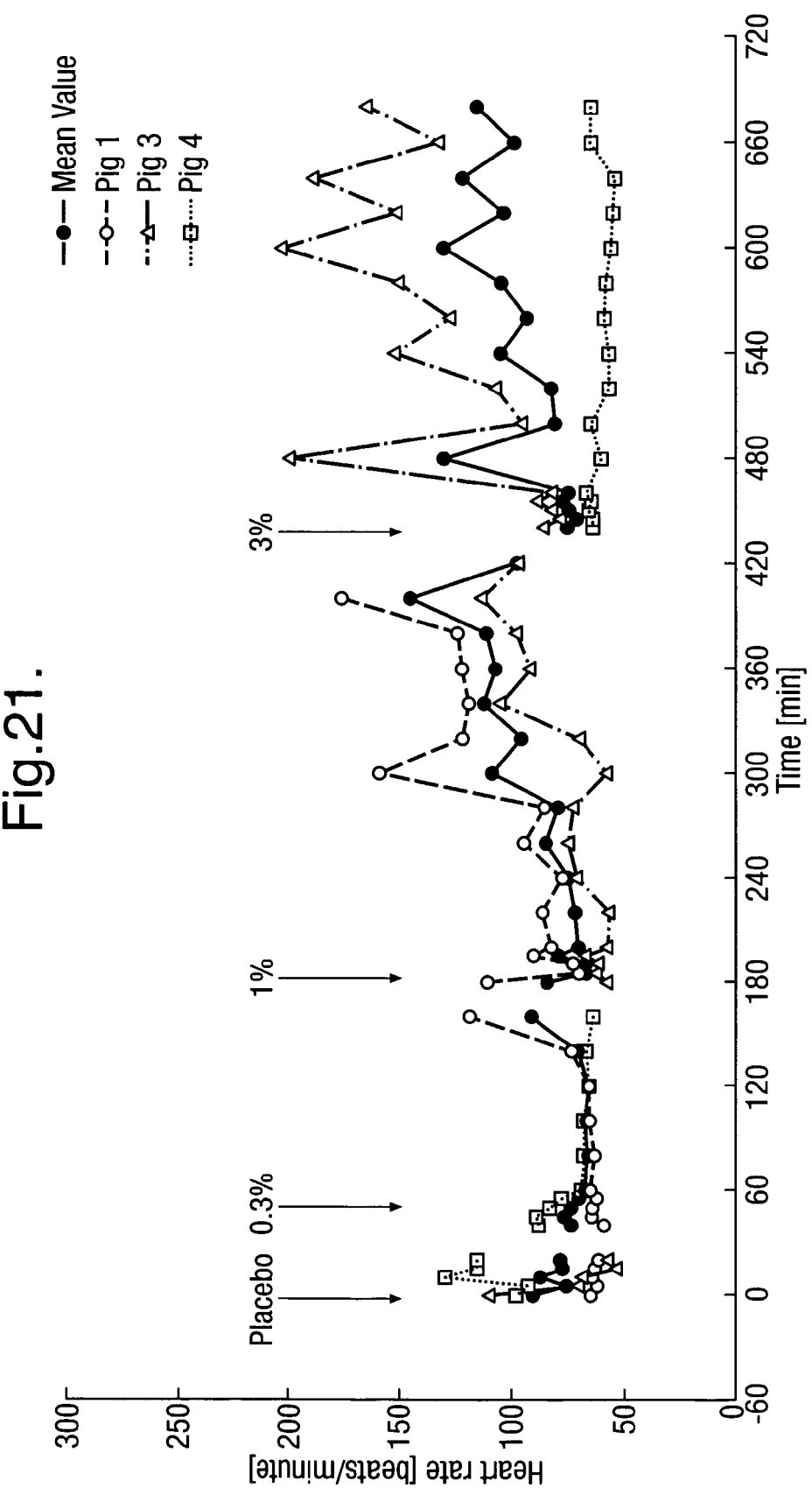
FIG. 21 shows the effect of 0.5 ml doses of placebo and of 0.3%, 1% and 3% w/w 1R,2S-methoxamine gels on the heart rate of pigs In each of FIGS. 17 to 21 the black circles are the mean values, the open circles are the values for pig 1, the open triangles are the values for pig 3, and the open squares are the values for pig 4.

Individual and mean values of the hear rate are presented in FIG. 21.

Reactivity of the Circulatory Functions

The expected reactions to arterenol or isoproterenol were not influenced by any of the 1R,2S-methoxamine gels.

Macroscopic Inspection

No pathological changes were observed following an application of 0.3%, 1%, or 3% 1R,2S-methoxamine.

Methoxamine Plasma Levels

The samples were analysed for the Methoxamine plasma levels. Dose-related plasma levels of Methoxamine were noted in all animals:

A dose level of 0.3% gel resulted in mean peak plasma levels of 4.90 and 6.97 ng/ml after 40 minutes.

A dose levels of 1.0% gel resulted in mean peak plasma levels of 9.88 and 11.0 ng/ml after 20 to 40 minutes.

A dose levels of 3.0% gel resulted in mean peak plasma levels of 50.4 and 61.3 ng/ml after 40 to 60 minutes.

There were little differences between the pigs.

CONCLUSIONS

The aim of this experiment was to assess the influence of 1R,2S-methoxamine on several cardiovascular parameters and on the mean anal resting pressure (MARP) in anaesthetised minipigs following topical administration to the anoderm.

0.5 ml of test substance were administered per animal by anodermal application as placebo, 0.3%, 1% or 3% 1R,2S-methoxamine (w/w).

An interval of at least 2 hours was employed between each application. The results were compared to the corresponding predose values.

Under the present test conditions treatment with 0.3%, 1%, or 3% 1R,2S-methoxamine led to no changes in cardiovascular parameters. A dose related increase in MARP was noted at all three concentrations:

A concentration of 0.3% 1R,2S-methoxamine caused an increase in MARP to 50 mmHg compared to the start values, a concentration of 1% caused an increase in MARP to 64 and a concentration of 3% caused an increase in MARP to 70 mmHg. Both animals were affected to a similar degree.

No influence was noted on the heart rate and ECG parameters P segment, P-Q interval, Q-T interval, QRS complex, and QTc-value. In particular, no evidence was noted for a prolongation of the Q-T interval. The expected reactions of the minipigs to arterenol and isoproterenol were not influenced.

During the macroscopical inspection no pathological changes were noted.

The methoxamine plasma levels reflected a dose-related exposure with maximum plasma levels of 6, 10 and 56 ng methoxamine/ml plasma for the 0.3%, 1% and 3% formulations, respectively. Maximum plasma levels were observed approximately 40 minutes following application. There were little difference between the pigs.

Pigs are an animal model known to be particularly relevant to humans. The results obtained above, demonstrating an increase in resting internal anal sphincter pressure on topical administration of 1R,2S-methoxamine at low concentrations and hence low doses, without local or systemic side effects, particularly without local irritation and without effects on blood pressure, are predictive of similar results in humans, and of the efficacy of topically administered 1R,2S-methoxamine in the treatment of faecal incontinence and analogous conditions, in particular those where an increase in sphincter tone is desired.

REFERENCES

[1] Nelson R, Norton N, Cautley E et al. Community-based prevalence of anal incontinence. JAMA 1995; 274:559-61.

[2] Kamm M A. Obstetric damage and faecal incontinence. Lancet 1994; 334:730-3.

[3] Vaizey C J, Kamm M A, Bartram C I. Primary degeneration of the internal anal sphincter.

[4] Jorge J M, Wexner S D. Etiology and management of fecal incontinence. Dis Colon Rectum 1993; 36:77-97.

[5] Mortensen N, Humphreys M S. The anal continence plug: a disposable device for patients with anorectal incontinence. Lancet 1991; 338:1163-5.

[6] Musial F, Enck P, Kalveram K T et al. The effect of loperamide on anorectal function in normal healthymen. J Clin Gastroenteral 1992; 15: 321-4.

[7] Cook T A, Mortensen N J Management of faecal incontinence following obstetric injury. Br J Surg 1998; 85:293-9.

[8] Deen K I, Kumar D, Williams J G et al. Randomized trial of internal anal sphincter application with pelvic floor repair for neuropathic fecal incontinence. Dis Colon Rectum 1995; 38:14-8.

[9] Vaizey C J, Kamm M A, Gold D M et al. Clinical, physiological and radiological study of a new purpose-designed artificial bowel sphincter. Lancet 1998; 353: 105-9.

[10] Maloug A J, Vaizey C J, Nicholls R J et al. Permanent sacral nerve stimulation for fecal incontinence. Ann Surg 2000; 232:143-8.

[11] Baeten C G, Konsten J, Spaans F et al. Dynamic graciloplasty for treatment of faecel incontinence. Lancet 1991; 338: 1163-5.

[12] Carapeti E A, Kamm M A, Evans B K et al. Topical phenylephrine increases anal sphincter resting pressure. Br J Surg 1999; 86: 267-70.

[13] Cheetham M J, Kamm M A, Phillips R K S. Topical phenylephrine increases anal canal resting pressure in patients with faecal incontinence. Gut 2001; 48:356-9.

[14] Speakman C T, Hoyle C H, Kamm M A et al. Adrenergic control of the internal anal sphincter is abnormal in patients with idiopathic faecal incontinence. Br J Surg 1990; 77:1342-4.

[15] Carapeti E A, Kamm M A, Phillips R K S. Ramdomized controlled trial of topical phenylephrine in the treatment of faecal incontinence. Br J Surg 2000: 87:38-42.

[16] Carapeti E A, Kamm M A, Nicholls R J et al. Randomized, controlled trial of topical phenylephrine for fecal incontinence in patients after ileoanal pouch construction. Dis Colon Rectum 2000; 43:1059-63.

[17] Fraunfelder F T, Scafidi A F. Possible adverse effects from topical ocular 10% phenylephrine. Am J Ophthalmol 1978; 85:447-53.

[18] Antibarro B, Barranco P, Ojeda J A. Allergic contact blepharoconjunctivitis caused by phenylephrine eyedrops. Contact Dermatitis 1991; 25:323-4.

[19] Brading A F, Sibley G N. A superfusion apparatus to study field stimulation of smooth muscle from mammalian urinary bladder. J Physiol 1983 334: 11-12P.

[20] Fujita M Hiyama T, Erythro-Directive Reduction of α-Substituted Alkanones by Means of Hydrosilanes in Acidic Media. J Org Chem 1988; 53: 5415-5421.

[21] Ward T J & Armstrong D W, Improved Cyclodextrin Chiral Phases: A Comparison & Review, J of Liq. Chrom. 9(2&3), 407-423 (1986).

We claim:

1. A pharmaceutical composition comprising isolated and purified 1R,2S-methoxamine or a physiologically tolerable salt thereof in admixture or conjunction with a pharmaceutically suitable carrier; said composition being in the form of a suppository.

2. A method of treating faecal incontinence, which comprises applying to a mammal in need thereof a pharmaceutical composition comprising isolated and purified 1R,2S-methoxamine or a physiologically tolerable salt thereof in admixture or conjunction with a pharmaceutically suitable carrier; said composition being in the form of a suppository.

3. A method of treating faecal incontinence, which comprises applying to a mammal in need thereof a pharmaceutical composition comprising isolated and purified 1R,2S-methoxamine or a physiologically tolerable salt thereof in admixture or conjunction with a pharmaceutically suitable carrier.

* * * * *